(12) United States Patent
Bogyo et al.

(10) Patent No.: US 10,570,173 B2
(45) Date of Patent: Feb. 25, 2020

(54) PROTEASE-ACTIVATED CONTRAST AGENTS FOR IN VIVO IMAGING

(71) Applicant: THE BOARD OF TRUSTEES OF THE LELAND STANFORD JUNIOR UNIVERSITY, Palo Alto, CA (US)

(72) Inventors: Matthew S. Bogyo, Redwood City, CA (US); Martijn Verdoes, Nijmegen (NL); Leslie Ofori, Jupiter, FL (US); Nimali P. Withana, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/545,689

(22) PCT Filed: Jan. 22, 2016

(86) PCT No.: PCT/US2016/014606
§ 371 (c)(1),
(2) Date: Jul. 22, 2017

(87) PCT Pub. No.: WO2016/118910
PCT Pub. Date: Jul. 28, 2016

(65) Prior Publication Data
US 2018/0002375 A1    Jan. 4, 2018

Related U.S. Application Data

(60) Provisional application No. 62/106,400, filed on Jan. 22, 2015.

(51) Int. Cl.
*A61K 49/00*    (2006.01)
*C07K 5/068*    (2006.01)
*A61K 51/08*    (2006.01)

(52) U.S. Cl.
CPC ...... *C07K 5/06086* (2013.01); *A61K 49/0056* (2013.01); *A61K 51/08* (2013.01)

(58) Field of Classification Search
CPC ...... A61K 51/00; A61K 51/08; A61K 51/088; A61K 38/00; A61K 49/00; A61K 49/0032; A61K 49/0034; A61K 49/0056; A61K 2121/00; A61K 2123/00; A61K 49/001; A61K 49/0013; A61K 49/0017; C07D 405/06; C07D 403/08; C07D 401/14; C07K 5/06086; C12Q 1/37

USPC ...... 424/1.11, 1.65, 1.69, 1.81, 1.85, 1.89, 424/9.1, 9.6; 514/1, 1.1; 530/300
See application file for complete search history.

(56) References Cited

U.S. PATENT DOCUMENTS

| 8,133,482 B2* | 3/2012 | Zheng ............... C07K 5/1008 |
| | | 424/9.61 |
| 9,845,493 B2* | 12/2017 | Brenner ............. C09B 29/0003 |
| 2006/0148014 A1 | 7/2006 | Agoulnik et al. |
| 2007/0036725 A1 | 2/2007 | Bogyo et al. |
| 2009/0252677 A1 | 10/2009 | Bogyo et al. |
| 2012/0329068 A1 | 12/2012 | Mao et al. |
| 2014/0180073 A1 | 6/2014 | Hiroshima et al. |
| 2014/0301950 A1 | 10/2014 | Lee et al. |

FOREIGN PATENT DOCUMENTS

| WO | 2004026344 A1 | 4/2004 |
| WO | 2012118715 A2 | 9/2012 |
| WO | 2013036743 A1 | 3/2013 |
| WO | 2014145257 A2 | 9/2014 |

OTHER PUBLICATIONS

Crisalli et al, Bioconjugate Chemistry, Nov. 16, 2011, No. 22, vol. 11, pp. 2345-2354 (Year: 2011).*
Verdoes et al. (2013) J. Am. Chem. Soc. 135 14726.
Ofori et al. (2015) ACS Chemical Biology 10 1977.
Withana et al. (2016) Scientific Reports 6 19755.
Lee and Bogyo (2010) ACS Chem. Biol. 5:233-43.
Blum et al. (2005) Nat. Chem. Biol. 1:203-9.
Blum et al. (2007) Nat. Chem. Bio. 3:668-677.
Verdoes et al. (2012) Chem. Biol. 19:619-28.
Watzke et al. (2008) Angew. Chem. Int. Ed. Engl. 47:406-9.
Hu et al. (2014) Angew. Chem. Int. Ed. Engl. 53:7669-73.
Kisin-Finfer et al. (2014) Bioorg. Med. Chem. Lett. 24:2453-8.
Chowdhury et al. (2014) J. Med. Chem. 57:6092-104.
Fujii et al. (2014) Bioconjug. Chem. 25:1838-46.
Mito et al. (2012) Cancer 118:5320-30.

\* cited by examiner

*Primary Examiner* — D. L. Jones
(74) *Attorney, Agent, or Firm* — David A. Roise; VLP Law Group LLP

(57) ABSTRACT

Compounds useful as contrast agents in image-guided surgery are provided. The compounds comprise a latent cationic lysosomotropic fragment that is detectable upon cleavage by lysosomal proteases within treated tissues, particularly within tumors and other diseased tissues. Also provided are compositions comprising the compounds and methods for using the compounds, for example in dynamically monitoring protease activity in vivo during image-guided tumor resection surgery.

10 Claims, 8 Drawing Sheets

(A)

cleavable amide bond substrate/non-covalent analogue probes

C (chromophore): Cy5

Q (quencher): QSY21-sulfo (2) 2CQ: R$_1$ = Cy5, R$_2$ = QSY21-sulfo, n = 2
(3) 4CQ: R$_1$ = Cy5, R$_2$ = QSY21-sulfo, n = 4
(4) 6CQ: R$_1$ = Cy5, R$_2$ = QSY21-sulfo, n = 6

(5) 2QC: R$_1$ = QSY21-sulfo, R$_2$ = Cy5, n = 2
(6) 4QC: R$_1$ = QSY21-sulfo, R$_2$ = Cy5, n = 4
(7) 6QC: R$_1$ = QSY21-sulfo, R$_2$ = Cy5, n = 6

(B)

*non-lysosomotropic effect*

*Latent lysosomotropic effect (LLE)*

Chromophore      Quencher      Protease

— Cat L  — Cat S  ⋯ Cat B  ⋯ Cat V  — Cat K (A)

PROTEASE-ACTIVATED CONTRAST AGENTS FOR IN VIVO IMAGING

CROSS-REFERENCE TO RELATED APPLICATIONS

This application is a national stage application of PCT International Application No. PCT/US2016/014606, filed Jan. 22, 2016, which claims the benefit of U.S. Provisional Application No. 62/106,400, filed on Jan. 22, 2015, the disclosures of which are incorporated herein by reference in their entireties.

STATEMENT OF GOVERNMENTAL SUPPORT

This invention was made with government support under project numbers R01 EB005011 and R01 HL116307, awarded by the National Institutes of Health. The government has certain rights in this invention.

BACKGROUND OF THE INVENTION

Surgical intervention is currently the most common treatment for virtually all types of solid tumors. Siegel et al. (2012) *CA Cancer J. Clin.* 62:220-41; DeSantis et al. (2014) *CA Cancer J. Clin.* 64:252-71. A successful outcome is therefore contingent upon the complete removal of all cancer cells from both the affected primary organ and from potential metastatic sites during surgery. Vahrmeijer et al. (2013) *Nat. Rev. Clin. Oncol.* 10:507-18. Contrast agents that target specific biomarkers in cancers can be used as intra-operative contrast agents to guide surgical resection of solid tumors in order to improve treatment outcome. Miwa et al. (2014) *J. Orthop. Res.* 32:1596-601; Fujita (2012) *J. Am. Coll. Surg.* 215:591. Among the diverse imaging modalities, optical based techniques utilizing fluorescent contrast agents have great potential. Rudin and Weissleder (2003) *Nat. Rev. Drug Discov.* 2:123-31; Bednar et al. (2007) *Expert Opin. Drug Discov.* 2:65-85. Indocyanine green (ICG), fluorescein, methylene blue, and 5-aminolevuliric acid (5-ALA) are all non-targeted contrast agents that are currently approved as injectable enhancers for the visualization of various tumors. Schaafsma et al. (2011) *J. Surg. Oncol.* 104:323-32; Tanaka et al. (2006) *Ann. Surg. Oncol.* 13:1671-81. In addition, several targeted contrast agents are in various stages of clinical development. Kovar et al. (2007) *Anal. Biochem.* 367: 1-12. Notably, an FITC probe that targets folate receptor-α was used in a clinical trial to demonstrate the value of intraoperative fluorescence-guided surgery (FGS) for the treatment of ovarian cancer. van Dam et al. (2011) *Nat. Med.* 17:1315-9. Additionally, other tumor-targeting agents, such as Chlorotoxin-Cy5.5, have been validated for optical imaging of malignant cancer cells using various mouse models of cancer. The mechanism of tumor selectivity for this agent is not, however, well understood. Veiseh et al. (2007) *Cancer Res.* 67:6882-8.

An alternative approach to general tumor-targeted contrast agents is the use of so called "smart probes" that only produce or accumulate a signal in tumor tissues when acted upon by an enzyme activity that is associated with the tumor or surrounding margins. One useful strategy in smart probe design is to make probes that produce signal when cleaved by a protease. Because proteases play significant roles in tumor growth and metastasis as well as in diverse pathologies such as fibrosis, inflammation, osteoporoses, and arthritis, contrast agents that are activated by proteases could prove valuable for the detection and treatment of many diseases. Turk (2006) *Nat. Rev. Drug Discov.* 5:785-99; Drag and Salvesen (2010) *Nat. Rev. Drug Discov.* 9:690-701.

A number of probes for tumor imaging applications have targeted the matrix metallo proteases (MMPs) due to their reported roles in angiogenesis and tumor growth. This includes both small molecule and large polymer-based probes that produce a signal upon cleavage as well as masked cell-penetrating peptides that accumulate inside cells when cleaved by an MMP. As an alternative to the MMPs, the cysteine cathepsins are important regulators of various aspects of tumorigenesis. Shree et al. (2011) *Genes Dev.* 25:2465-79. These proteases are also highly expressed and activated in many cells that regulate the intrinsic inflammatory response. Mohamed and Sloane (2006) *Nat. Rev. Cancer* 6:764-75. In general, cysteine cathepsin activities are elevated in virtually all solid tumors due to increased infiltration of immune cells. Mitchem et al. (2013) *Cancer Res.* 73:1128-41; McIntyre and Matrisian (2003) *J. Cell. Biochem.* 90:1087-97; Fonovic and Bogyo (2007) *Curr. Pharm. Des.* 13:253-61; Gocheva et al. (2010) *Genes Dev.* 24:241-55. The cysteine cathepsins have therefore been targeted in the design of tumor-specific contrast imaging agents. Such agents include fluorescent activity-based probes that covalently modify the cathepsins during turnover (Verdoes et al. (2013) *J. Am. Chem. Soc.* 135:14726-30; Lee and Bogyo (2010) *ACS Chem. Biol.* 5:233-43; Blum et al. (2005) *Nat. Chem. Biol.* 1:203-9; Blum et al. (2007) *Nat. Chem. Bio.* 3:668-677; Verdoes et al. (2012) *Chem. Biol.* 19:619-28), a range of high and low molecular weight quenched substrate probes (Watzke et al. (2008) *Angew. Chem. Int. Ed. Engl.* 47:406-9; Hu et al. (2014) *Angew. Chem. Int. Ed. Engl.* 53:7669-73), and fluorogenic turn-on substrate probes (Kisin-Finfer et al. (2014) *Bioorg. Med. Chem. Lett.* 24:2453-8; Chowdhury et al. (2014) *J. Med. Chem.* 57:6092-104; Fujii et al. (2014) *Bioconjug. Chem.* 25:1838-46). Although all of the reported protease-triggered smart probes have proven useful for imaging of tumor margins in mouse models of cancer (Verdoes et al. (2013) *J. Am. Chem. Soc.* 135:14726-30; Hu et al. (2014) *Angew. Chem. Int. Ed. Engl.* 53:7669-73; Mito et al. (2012) *Cancer* 118:5320-30), all have limitations in terms of tumor contrast and none have been used with clinically-approved imaging instrumentation. Furthermore, most have only been validated using simple graft models of cancer in which large tumors are imaged at or near the skin surface. Therefore, the optimization of a targeted contrast agent with enhanced contrast for multiple tumor types and that could be used with existing clinical instrumentation within the confines of existing surgical workflows would be transformative to many surgical procedures.

Methods and materials for the imaging of cells containing active proteases such as cathepsins are disclosed in U.S. Patent Application Publication No. 2007/0036725. Radiolabeled activity-based probes useful in the radiolabeling of target enzymes, including cathepsins, in vivo are disclosed in U.S. Patent Application Publication No. 2009/0252677. In each of cases, the probes employ an ester-linked acyloxymethyl ketone (AOMK) reactive group to modify the protease active site covalently. Non-peptidic activity-based fluorescent probes are disclosed in PCT International Publication No. WO 2012/118715.

PCT International Publication No. WO 2014/145257 discloses quenched ABPs comprising an ether-linked, 2,3,5,6-tetrafluoro-substituted phenoxymethyl ketone (PMK) leaving element. The detectable component of the disclosed ABPs remain covalently attached to their target protease after enzymatic turnover.

U.S. Patent Application Publication No. 2014/0301950 discloses imaging agents comprising a dark quencher, an amino acid backbone, a fluorophore, 6-aminohexanoic acid, aminoethoxyethoxyacetyl spacers, and a methoxypolyethylene glycol (mPEG) chain. The agents are purportedly cleaved by cathepsins to generate a fluorescent signal and thus to image diseased cells. The technology is directed at identifying diseased cells at or near the surface of a tissue.

Despite these disclosures, there remains a need in the field for novel activity-based contrast agents that have high cellular uptake, that target a broad spectrum of animal proteases, and that offer increased sensitivity of detection at a variety of wavelengths, particularly at wavelengths capable of penetrating diseased tissue.

SUMMARY OF THE INVENTION

The present invention addresses these and other needs by providing compounds, compositions, and methods of use of the compounds and compositions that target animal proteases. In particular, according to one aspect of the invention, compounds are provided as represented by structural formula (I):

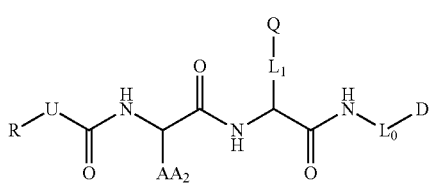

wherein D is a detectable element comprising a fluorescent label;
Q is a quencher;
$L_0$ and $L_1$ are linkers;
$AA_2$ is an amino acid side chain;
U is O, N, or S;
R is alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or a protecting group, and is optionally substituted with 1 to 3 A groups; and each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido.

In some compound embodiments of formula (I), the fluorescent label is a fluorescein, an Oregon green, a boradiaza-indecene, a rhodamine, or a cyanine label. Specifically, the fluorescent label may be a cyanine label, and more specifically, the cyanine label may be Cy5.

In some embodiments of formula (I), the fluorescent label is a near infrared fluorescent label. For example, the near infrared fluorescent label may be a benzopyrillium or cyanine label, and more specifically, the benzopyrillium or cyanine label may be a DyLight label.

In some embodiments, $AA_2$ is an aralkyl amino acid side chain, optionally substituted with 1 to 3 A groups, and in some embodiments, U is O. In some embodiments, $L_0$ and $L_1$ is each independently an optionally substituted alkyl linker, wherein each carbon atom is optionally replaced with a heteroatom. In specific embodiments, $L_0$ and $L_1$ is each independently a $C_{2-8}$ alkyl linker. Even more specifically, $L_1$ is a $C_4$ alkyl linker.

In some embodiments, Q is a QSY quencher, more specifically a hydrophilic QSY quencher, and even more specifically the hydrophilic QSY quencher is a sulfo-QSY quencher. In other specific embodiments, Q is QC-1.

According to some embodiments, the compounds of the invention have structural formula (II):

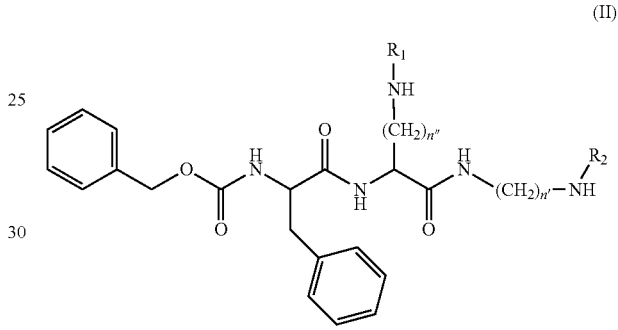

wherein
n' and n" is each independently an integer from 2-8;
$R_1$ is a QSY quencher or QC-1; and
$R_2$ is a benzopyrillium or cyanine label.
More specifically, n' may be 2, 4, or 6, or n" may be 4. Even more specifically, n' is 2, 4, or 6, and n" is 4
In some embodiments, the compound is selected from the group consisting of any of the following compounds:

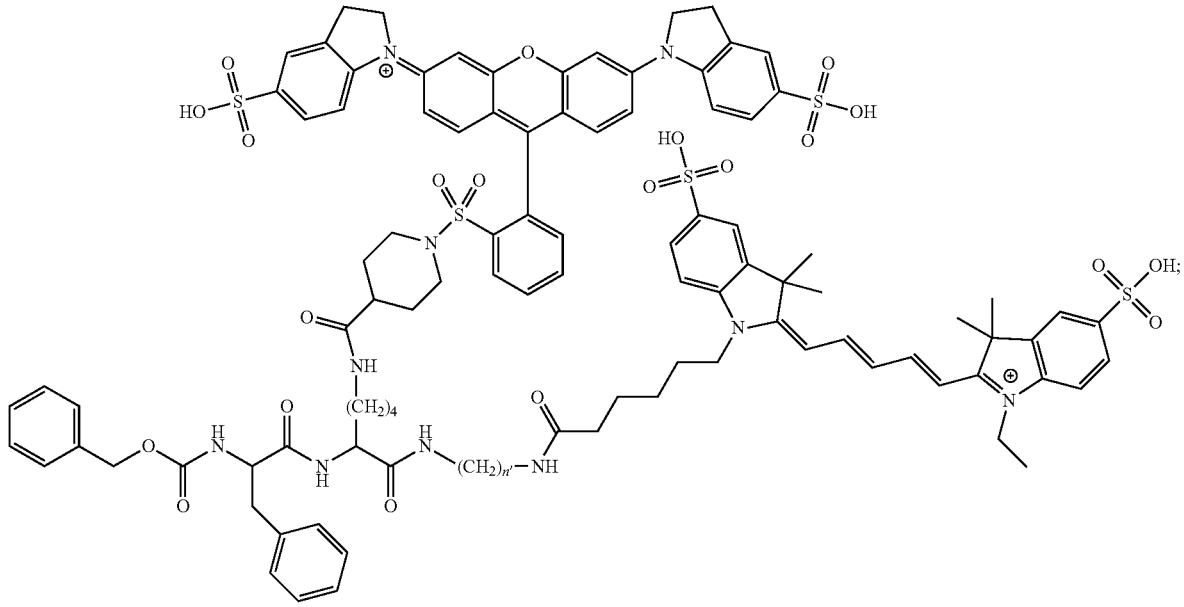

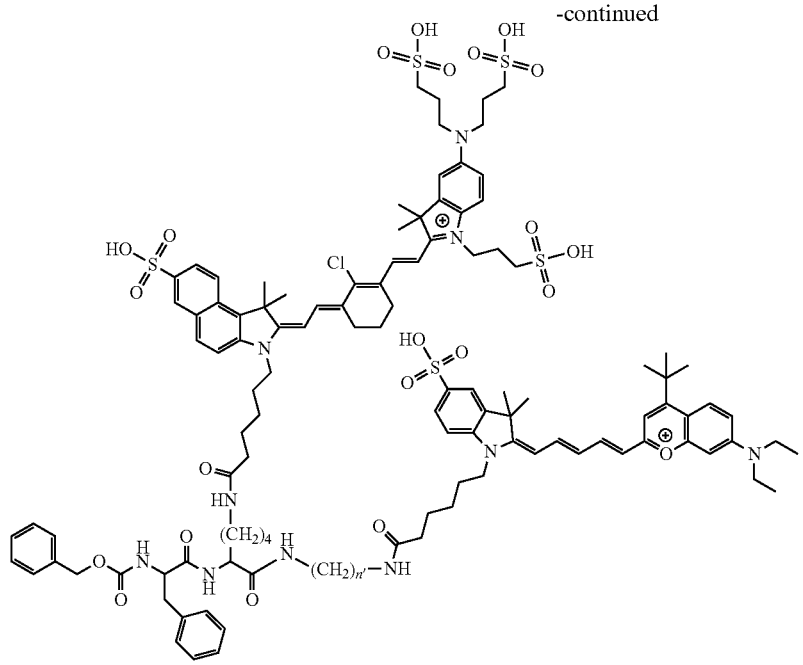

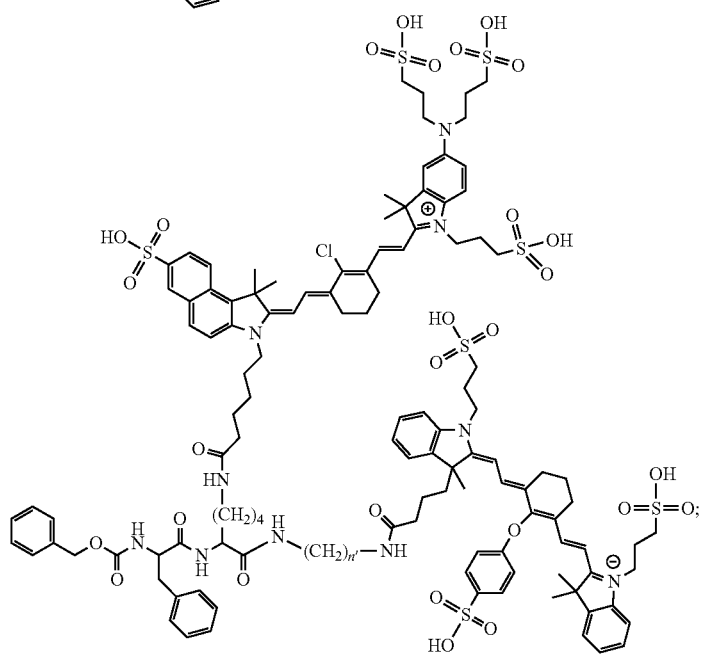

wherein n' is 2, 4, or 6; or pharmaceutically acceptable salts of those compounds.

In another aspect of the invention, compounds are provided as represented by structural formula (III):

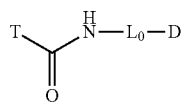

wherein
D is a detectable element;
L₀ is a linker; and

T is a protease targeting element, optionally comprising a quencher;

provided that L₀ does not comprise an ethoxyethoxy spacer.

According to some compound embodiments having the structure of formula (III), D comprises a fluorescent label and T comprises a quencher.

In specific embodiments, the fluorescent label is a fluorescein, an Oregon green, a bora-diaza-indecene, a rhodamine, or a cyanine label. More specifically, the fluorescent label is a cyanine label, and even more specifically, the cyanine label is Cy5.

In some embodiments, the fluorescent label is a near infrared fluorescent label. Specifically, the near infrared fluorescent label may be a benzopyrillium or cyanine label. More specifically, the benzopyrillium or cyanine label may be a DyLight label.

In some embodiments of formula (III), D comprises a radioactive substance.

In some embodiments of formula (III), $L_0$ is an optionally substituted alkyl linker, wherein each carbon atom is optionally replaced with a heteroatom. Specifically, $L_0$ may be a $C_{2-8}$ alkyl linker.

In some compound embodiments where D comprises a fluorescent label and T comprises a quencher, the quencher may be a QSY quencher. Specifically, the QSY quencher may be a hydrophilic QSY quencher, and more specifically, the hydrophilic QSY quencher may be a sulfo-QSY quencher. In some embodiments where D comprises a fluorescent label and T comprises a quencher, the quencher is QC-1.

In some embodiments of formula (III), T is a peptidic targeting element. In specific embodiments, T contains no more than four amino acid residues. In some embodiments, T is a cathepsin targeting element, optionally comprising a quencher. More specifically, T may be selective for cathepsin L or cathepsin V.

In some embodiments of formula (III), T is

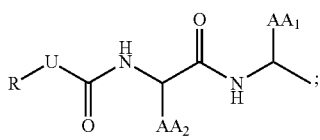

$AA_1$ and $AA_2$ is each independently an amino acid side chain;

U is O, N, or S;

R is alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or a protecting group, and is optionally substituted with 1 to 3 A groups; and each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido.

In specific embodiments, $AA_1$ is a basic amino acid side chain and $AA_2$ is an aralkyl amino acid side chain, each optionally substituted with 1 to 3 A groups.

In other specific embodiments, U is O. In still other specific embodiments, D comprises a fluorescent label and T comprises a quencher. More specifically, the fluorescent label may be a fluorescein, an Oregon green, a bora-diaza-indecene, a rhodamine, or a cyanine label. Even more specifically, the fluorescent label may be a cyanine label, such as Cy5. In some specific embodiments, the fluorescent label may be a near infrared fluorescent label, such as a benzopyrillium or cyanine label, for example a DyLight label.

In some embodiments of formula (III) where T is

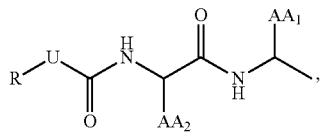

D comprises a radioactive substance.

In some embodiments of formula (III) where T is

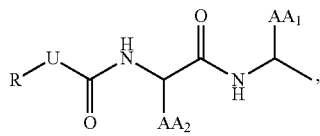

and where D comprises a fluorescent label, $AA_1$ comprises a quencher. More specifically, $AA_1$ may be $-L_1-Q$, wherein $L_1$ is a linker and Q is the quencher. In these embodiments, $L_1$ may more specifically be an optionally substituted alkyl linker, wherein each carbon atom is optionally replaced with a heteroatom. Even more specifically, $L_1$ may be a $C_{2-8}$ alkyl linker such as a $C_4$ alkyl linker.

In some of the above compounds of formula (III), $AA_2$ is an aralkyl amino acid side chain, optionally substituted with 1 to 3 A groups. In some of these compounds, U is O. In some of the above compounds, Q is a QSY quencher, such as a hydrophilic QSY quencher, or even a sulfo-QSY quencher.

In another aspect, the invention provides compositions for use in labeling a tissue in an animal. These compositions comprise any of the above compounds and a pharmaceutically acceptable carrier.

In yet another aspect, the invention provides methods of labeling a tissue in an animal. These methods comprise the step of administering any of the above compositions to the animal.

In still yet another aspect, the invention provides methods of visualizing a tumor in an animal. The methods comprise the steps of:

administering any of the above compositions to the animal; and measuring a detectable signal generated in the animal from a reaction of the composition with a cathepsin cysteine protease;

wherein the detectable signal is associated with a diseased tissue in the animal.

In embodiments, the detectable signal is a fluorescent signal. More specifically, the fluorescent signal is a near infrared signal.

In other embodiments, the detectable signal is generated at a tumor margin.

In still other embodiments, the detectable signal is measured using an image-guided surgical device.

DETAILED DESCRIPTION OF THE INVENTION

The instant specification discloses inter alia the design and optimization of quenched fluorescent substrate probes for use in non-invasive imaging applications. In particular, modified peptides are provided that contain either a quencher and fluorophore pair or a radioisotope label. The compounds release a fragment upon protease cleavage that contains the reporter (either the unquenched fluorophore or the radioisotope) and a protonable amine, thus resulting in enhanced lysosome retention of the released fragment.

The compounds of the invention are useful for contrast imaging in any conditions that involve inflammation. The compounds find particular use in image-guided surgery of various solid tumors (breast, colon, lung, etc.), but are also useful in diagnosing and monitoring atherosclerosis, fibrosis, infectious diseases (e.g., tuberculosis infections), and any condition where cathepsins, or other proteases, are secreted in an inflammatory response.

Previous examples of activity-based probes (ABPs) known to target cysteine proteases include a series of quenched near-infrared fluorescent activity-based probes (qNIRF-ABPs) that covalently target the papain-family of cysteine proteases (Blum et al. (2007) *Nat. Chem. Bio.* 3:668-677) and a series of potent cysteine protease-selective ABP compounds having ether-linked leaving groups (Verdoes et al. (2013) *J. Am. Chem. Soc.* 135:14726-30; PCT International Publication No. WO2014/145257). The previous ABPs result in the covalent modification of the protease active site by the reactive probe during enzyme turnover. The fluorescent label remains covalently attached to the protease, and its latent fluorescence is unmasked by release of the portion of the probe containing the quencher during enzyme turnover.

Figure 1:
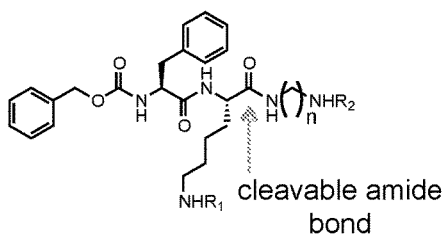
FIG. 1A-FIG. 1C. Design of cathepsin-selective protease substrate probes. (A) Chemical structures of six substrate analogs having a protease-cleavable amide bond. In the structures designated "nCQ" (compounds 2-4), where the "n" value corresponds to spacer length (n=2, 4, and 6), the chromophore (C) is attached to the lysine side chain ($R_1$) whereas in the structures designated "nQC" (compounds 5-7), the value of "n" also corresponds to space length, but the chromophore is attached to the amine group on the C-terminal side of the cleavable amide bond ($R_2$). (B) Schematic representation of the latent lysosomotropic effect (LLE) introduced into the probe design in order to improved retention of the cleaved fluorescent products of probe cleavage.
Figure 1:
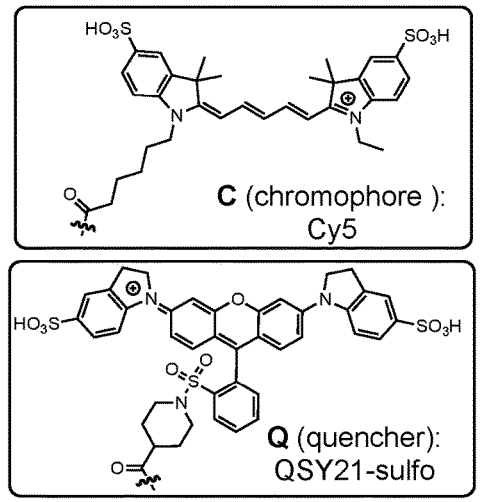
Figure 1:
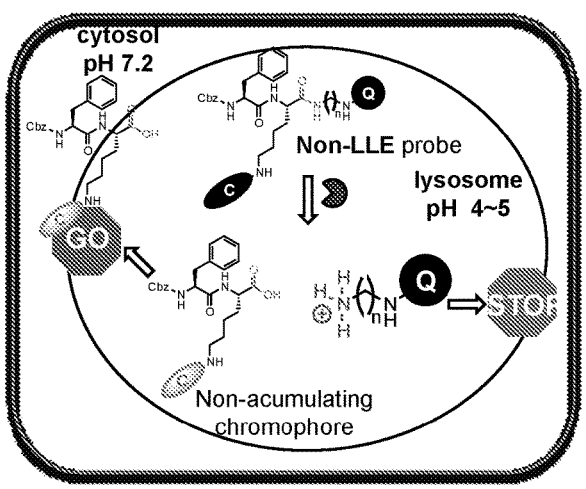
Figure 1:
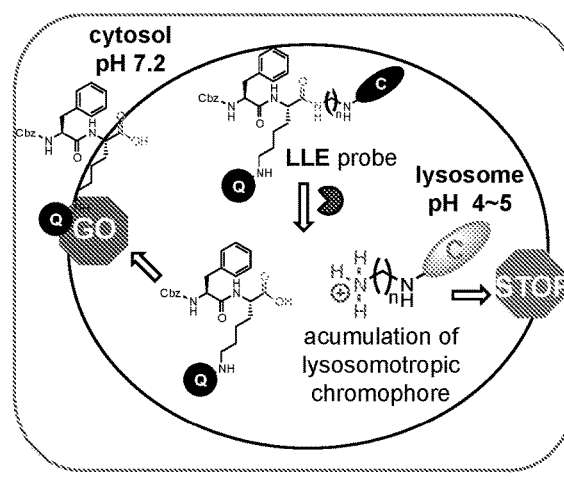
Figure 1:
Figure 1:
Figure 1:

The current probes are a novel variation of the inventors' existing ABPs (Verdoes et al. (2013) *J. Am. Chem. Soc.* 135:14726-30; PCT International Publication No. WO2014/145257) in which the PMK warhead has been replaced by a native amide bond that is cleavable by a protease (FIG. 1A). The length of the alkyl spacer between the substrate and the cleavage group has been varied in the new substrates, and the effects of placing the reporter fluorophore and the quencher in different locations on the substrates has been assessed. Without intending to be bound by theory, it is believed that protonation of the free amino group of the cleaved substrate fragment in lysosomes (pH~4-5) reduces the diffusion rate of the cationic intermediate across the lysosomal membrane (Soulet et al. (2004) *J. Biol. Chem.* 279:49355-66), thus enhancing retention of the cleaved fragment in lysosomes and thereby increasing the strength of the signals and prolonging the duration in tumors for substrates containing a fluorophore on the cleaved fragment. See also Kazmi et al. (2013) 41:897-905.

In vitro enzyme kinetic analysis showed that the designed substrates are efficiently cleaved (unquenched) by various cysteine cathepsins, particularly by cathepsin L. Turnover numbers and affinity for the substrates are comparable to commercial substrates for cysteine cathepsins. In noninvasive imaging studies using a syngeneic orthotopic mouse model of breast cancer it was found that the designed substrate probes have ideal pharmacological properties, such as fast labeling kinetics, significant accumulation in tumors and areas around tumors, followed by fast clearance from organs. These results confirm that it is possible to increase signal intensity and overall contrast by the introduction of a latent cationic tropism into the probe design.

Compounds

Accordingly, in one aspect, the instant disclosure provides novel compounds for use as imaging agents in the detection and imaging of protease activity, particularly the activity of cathepsins in animal tissues. In some embodiments, the compounds have formula (I):

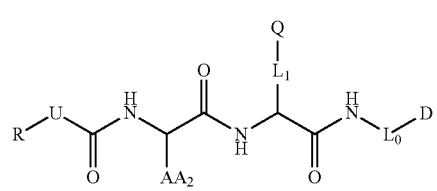

(I)

wherein D is a detectable element comprising a fluorescent label;
Q is a quencher;
$L_0$ and $L_1$ are linkers;
$AA_2$ is an amino acid side chain;
U is O, N, or S;
R is alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or a protecting group, and is optionally substituted with 1 to 3 A groups; and
each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido.

As used herein, the term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In some embodiments, a straight chain or branched chain alkyl has 30 or fewer carbon atoms in its backbone (e.g., $C_1$-$C_{30}$ for straight chains, $C_3$-$C_{30}$ for branched chains), and more specifically 20 or fewer. Likewise, some cycloalkyls have from 3-10 carbon atoms in their ring structure, and more specifically have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halo, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a thio, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

As used herein, the term "alkoxy" refers to an alkyl group, in certain specific embodiments, a lower alkyl group, having an oxygen attached thereto. Representative alkoxy groups include methoxy, ethoxy, propoxy, t-butoxy, and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed above, except where stability is prohibitive. For example, substitution of alkenyl groups by one or more alkyl, cycloalkyl, heterocyclyl, aryl, or heteroaryl groups is contemplated.

The term "$C_{x\text{-}y}$" when used in conjunction with a chemical moiety, such as acyl, acyloxy, alkyl, alkenyl, alkynyl, or alkoxy, is meant to include groups that contain from x to y carbons in the chain. For example, the term "$C_{x\text{-}y}$-alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. "$C_0$-alkyl" indicates a hydrogen where the group is in a terminal position, or is a bond if internal. The terms "$C_{2\text{-}y}$-alkenyl" and "$C_{2\text{-}y}$-alkynyl" refer to substituted or unsubstituted unsaturated aliphatic groups analogous in length and possible substitution to the alkyls described above, but that contain at least one double or triple bond, respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, cycloalkyl, heterocyclyl, aryl, or heteroaryl groups is contemplated.

The term "amide", as used herein, refers to a group

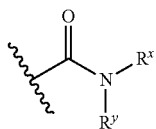

wherein $R^x$ and $R^y$ each independently represent a hydrogen or hydrocarbyl group, or $R^x$ and $R^y$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

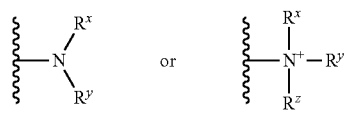

wherein $R^x$, $R^y$, and $R^z$ each independently represent a hydrogen or a hydrocarbyl group, or $R^x$ and $R^y$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted single-ring aromatic groups in which each atom of the ring is carbon. In certain embodiments, the ring is a 5- to 7-membered ring, and in more specific embodiments is a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

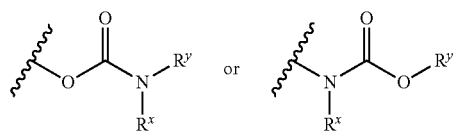

wherein $R^x$ and $R^y$ independently represent hydrogen or a hydrocarbyl group, or $R^x$ and $R^y$ taken together with the atoms to which they are attached complete a heterocycle having from 4 to 8 atoms in the ring structure.

The term "cycloalkyl", as used herein, refers to a non-aromatic saturated or unsaturated ring in which each atom of the ring is carbon. In certain embodiments, a cycloalkyl ring contains from 3 to 10 atoms, and in more specific embodiments from 5 to 7 atoms.

The term "carbonate" is art-recognized and refers to a group —OCO$_2$—R$^x$, wherein R$^x$ represents a hydrocarbyl group.

The term "carboxy", as used herein, refers to a group represented by the formula —CO$_2$H.

The term "ester", as used herein, refers to a group —C(O)OR$^x$ wherein R$^x$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "guanidinyl" is art-recognized and may be represented by the general formula

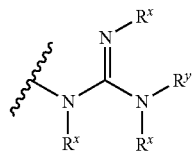

wherein $R^x$ and $R^y$ independently represent hydrogen or a hydrocarbyl.

The terms "halo" and "halogen" as used herein mean halogen and include chloro, fluoro, bromo, and iodo.

The terms "hetaralkyl" and "heteroaralkyl", as used herein, refer to an alkyl group substituted with a hetaryl group.

The terms "heteroaryl" and "hetaryl" include substituted or unsubstituted aromatic single ring structures, in certain specific embodiments 5- to 7-membered rings, more specifically 5- to 6-membered rings, whose ring structures include at least one heteroatom, in some embodiments one to four heteroatoms, and in more specific embodiments one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Typical heteroatoms are nitrogen, oxygen, and sulfur.

The terms "heterocyclyl", "heterocycle", and "heterocyclic" refer to substituted or unsubstituted non-aromatic ring structures, in certain specific embodiments 3- to 10-membered rings, more specifically 3- to 7-membered rings, whose ring structures include at least one heteroatom, in some embodiments one to four heteroatoms, and in more specific embodiments one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes herein, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as acyl, acyloxy, alkyl, alkenyl, alkynyl, or alkoxy is meant to include groups where there are ten or fewer non-hydrogen atoms in the substituent, and in certain embodiments, six or fewer. A "lower alkyl", for example, refers to an alkyl group that contains ten or fewer carbon atoms, and in specific embodiments six or fewer carbon atoms. In certain embodiments, the acyl, acyloxy, alkyl, alkenyl, alkynyl, and alkoxy substituents defined herein are respectively lower acyl, lower acyloxy, lower alkyl, lower alkenyl, lower alkynyl, and lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, more specifically from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc., under conditions in which the compound is to be used. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

Unless specifically described as "unsubstituted", references to chemical moieties herein are understood to include substituted variants. For example, reference to an "aryl" group or moiety implicitly includes both substituted and unsubstituted variants.

The term "sulfate" is art-recognized and refers to the group —OSO₃H, or a pharmaceutically acceptable salt thereof.

The term "sulfonamide" is art-recognized and refers to the group represented by the general formulae

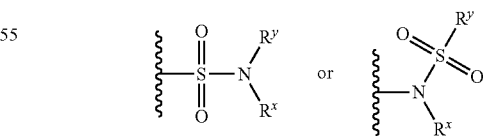

wherein $R^x$ and $R^y$ independently represent hydrogen or hydrocarbyl.

The term "sulfoxide" is art-recognized and refers to the group —S(O)—$R^x$, wherein $R^x$ represents a hydrocarbyl.

The term "sulfo" or "sulfonate" is art-recognized and refers to the group —SO₃H, or a pharmaceutically acceptable salt thereof.

The term "sulfone" is art-recognized and refers to the group —S(O)$_2$—R$^x$, wherein R$^x$ represents a hydrocarbyl.

The term "thioalkyl", as used herein, refers to an alkyl group substituted with a thiol group.

The term "thioester", as used herein, refers to a group —C(O)SR$^x$ or —SC(O)R$^x$ wherein R$^x$ represents a hydrocarbyl.

The term "thioether", as used herein, is equivalent to an ether, wherein the oxygen is replaced with a sulfur.

The term "urea" is art-recognized and may be represented by the general formula

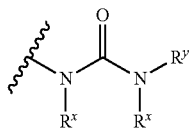

wherein R$^x$ and R$^y$ independently represent hydrogen or a hydrocarbyl.

The compounds of the instant invention are generally synthesized using standard synthetic chemical techniques, for example using the methods described in the Examples section below. Other useful synthetic techniques are described, for example, in *March's Advanced Organic Chemistry: Reactions, Mechanisms, and Structure*, 7th Ed., (Wiley, 2013); Carey and Sundberg, *Advanced Organic Chemistry* 4$^{th}$ Ed., Vols. A and B (Plenum 2000, 2001); *Fiesers' Reagents for Organic Synthesis, Volumes* 1-27 (Wiley, 2013); *Rodd's Chemistry of Carbon Compounds, Volumes* 1-5 *and Supplementals* (Elsevier Science Publishers, 1989); *Organic Reactions, Volumes* 1-81 (Wiley, 2013); and *Larock's Comprehensive Organic Transformations* (VCH Publishers Inc., 1989) (all of which are incorporated by reference in their entirety). The compounds are normally synthesized using starting materials that are generally available from commercial sources or are readily prepared using methods well known to those skilled in the art. See, e.g., *Fiesers' Reagents for Organic Synthesis, Volumes* 1-27 (Wiley, 2013), or *Beilsteins Handbuch der organischen Chemie*, 4, *Aufl.* ed. Springer-Verlag, Berlin, including supplements.

When referring to components of the compounds of the invention, the term "residue derived from" may be used to describe a residue formed by the reaction of a first reactive functional group on a first component and a second reactive functional group on a second component to form a covalent bond. In exemplary embodiments, an amine group on a first component may be reacted with an activated carboxyl group on a second component to form a residue including one or more amide moieties. Other permutations of first and second reactive functional groups are encompassed by the invention. For example, the copper-catalyzed or copper-free reaction of an azide-substituted first component with an alkyne-substituted second component results in a triazole-containing residue through the well-known "click" reaction, as would be understood by those of ordinary skill in the art. See Kolb et al. (2001) *Angew. Chem. Int. Ed. Engl.* 40:2004; Evans (2007) *Aus. J. Chem.* 60:384. Exemplary methods of generating non-peptidic fluorescent imaging probes using "click" reactions are provided in PCT International Publication No. WO 2012/118715. Adaptation of these methods to generate or modify compounds of the instant claims, in particular the protease targeting element of the instant compounds, is within the skill in the art.

One of ordinary skill in the art would understand that a protecting group is reversibly attached to a desired position of the molecule to control the reaction of other agents at that position. Protecting groups useful in the synthesis of the instant compounds are well known in the art. See, for example, *Greene's Protective Groups in Organic Synthesis*, 4$^{th}$ *edition*, by P. G. M. Wuts and T. W. Greene (Wiley-Interscience, 2006); and *Protecting Groups*, by P. Kocienski (Thieme, 2005).

The L$_0$ and L$_1$ groups of the instant compounds are linker groups that connect the detectable element, D, and the quencher, Q, respectively, to the subject compounds. Each linker group may independently be any suitable chemical linker, as would be understood by the person of ordinary skill in the art. The L$_0$ and L$_1$ groups are preferably alkyl linker groups, wherein the alkyl linker is optionally substituted, and furthermore, wherein the carbons in the linker are optionally replaced by heteroatoms to the extent that the resulting structure is chemically stable. Such substitutions and replacements should be understood to include intervening groups within the linker such as ethers, thioethers, disulfides, esters, amides, carbonates, carbamates, and so forth. Preferred linkers range in length from 5 to 40 bonds and may be branched, straight-chain, or contain rings. Linkers may in some cases include double bonds. They may be hydrophobic or hydrophilic as desired, according to the particular requirements of the compound containing the linker.

In specific embodiments, L$_0$ and L$_1$ is each independently an optionally substituted alkyl linker, wherein each carbon atom is optionally replaced with a heteroatom. In more specific embodiments, L$_0$ and L$_1$ is each independently a C$_{2-8}$ alkyl linker. In even more specific embodiments, L$_1$ is a C$_4$ alkyl linker.

It should further be understood that the connection between the L$_0$ group and the detectable element, D, and between the L$_1$ group and the quencher, Q, may be any suitable chemical connection, as would be understood by the skilled artisan. For example, the instant compounds may in some cases be conveniently prepared by including in the delectable element or quencher precursor a moiety that is reactive with a particular chemical group, such as, for example, an amino group, a thiol group, or the like. The reactive detectable element or quencher can in such a situation be readily attached to the compound through the reaction of the amino group, the thiol group, or the like on the compound with the reactive group. These types of chemical connections are thus understood to be within the scope of the disclosed compounds, even if the structural details of the connection are not explicitly shown.

According to some embodiments, the L$_1$ group in compounds of formula (I) may be modified to increase the half-life of the subject compounds in vivo. In these embodiments, the L$_1$ group may therefore comprise a polyethylene glycol moiety, a palmitate or other long-chain fatty acid moiety, an albumin binding protein, or the like, in order to stabilize the modified compounds.

The AA$_1$ and AA$_2$ groups of the instant compounds may independently be any natural or unnatural amino acid side chain, as would be understood by the skilled artisan, or may be the group "-L$_1$-Q". In some embodiments, the AA$_1$ group is a basic amino acid side chain and the AA$_2$ group is an aralkyl amino acid side chain, and each is optionally substituted with 1 to 3 A groups. In specific embodiments, the AA$_1$ group is a lysine side chain and the AA$_2$ group is a phenylalanine side chain. In some embodiments, the AA$_1$ group is -L$_1$-Q and the AA$_2$ group is an aralkyl amino acid side chain. In other embodiments, the $AA_1$ group is a basic amino acid side chain and the $AA_2$ group is -$L_1$-Q. In still other embodiments, the $AA_1$ and $AA_2$ groups are independently a side chain from an acidic amino acid residue, such as a side chain from an aspartic acid or glutamic acid residue, or a side chain from an alkyl amino acid residue, such as an alanine, leucine, isoleucine, valine, or other such amino acid residue, in any combination. Side chains from other amino acid residues, such as lysine, arginine, tyrosine, glutamine, asparagine, and the like, are also suitable as either $AA_1$ or $AA_2$ groups in the instant compounds.

In compound embodiments where the $AA_1$ or $AA_2$ group is an "-$L_1$-Q" group, the $L_1$ linker component may be provided by an amino acid side chain. For example, a lysine residue conveniently provides an amino-alkyl group for reaction with a suitably activated quencher.

In some compound embodiments, the U group is O.

In some compound embodiments, the R group is an alkyl group that is optionally substituted with 1 to 3 A groups. More specifically, the R group may be an alkyl group that is substituted with aryl that is itself optionally substituted. Even more specifically, the R group may be an optionally substituted aralkyl group such as, for example, a benzyl group.

The detectable element, D, of the instant compounds is any chemical group capable of being detected by any suitable means, including without limit, optical, electrical, or chemical detection methods. In specific embodiments, the detectable element is a fluorescent label, a luminescent species, a phosphorescent species, a radioactive substance, including a positron-emitting substance, a nanoparticle, a SERS nanoparticle, a quantum dot or other fluorescent crystalline nanoparticle, a diffracting particle, a Raman particle, a metal particle, including a chelated metal, a magnetic particle, a microsphere, an RFID tag, a microbarcode particle, or a combination of these labels. In more specific embodiments, the detectable element is a fluorescent label, a radiolabel, including a chelated metal, and the like. Examples of radiolabels and chelated metals suitable for use in these compounds are described in PCT International Publication No. 2009/124265, which is hereby incorporated by reference herein in its entirety.

In preferred embodiments of the instant compounds, the detectable element is a fluorescent label. As is known by those of ordinary skill in the art, fluorescent labels emit electromagnetic radiation, preferably visible light or near infrared light, when stimulated by the absorption of incident electromagnetic radiation. A wide variety of fluorescent labels, including labels having reactive moieties useful for coupling the label to reactive groups such as, for example amino groups, thiol groups, and the like, are commercially available. See, e.g., *The Molecular Probes® Handbook—A Guide to Fluorescent Probes and Labeling Technologies*, Life Technologies, Thermo Fisher Scientific. Other useful fluorescent reagents, including a variety of near infrared (NIR) fluorescent labels, are available from Thermo Scientific Pierce Protein Biology Products, Rockford, Ill.

Near infrared fluorophores, which typically absorb in the region of 700-900 nm are particularly suitable for tissue imaging, as light of these wavelengths is capable of penetrating more deeply into tissues than light of shorter, for example visible, wavelengths. Exemplary near infrared fluorescent labels usefully employed in the compounds of the instant invention are the IRDye infrared dyes available from LI-COR Biosciences, Lincoln, Nebr. Non-limiting examples of these dyes are IRDye 800CW, IRDye 680RD, IRDye 680LT, IRDye 750, IRDye 700DX, IRDye 800RS, and IRDye 650.

Other examples of infrared dyes that are particularly well suited for in vivo imaging applications are the DyLight series of benzopyrillium and benzocyanine compounds, which are available from Thermo Scientific Pierce Protein Biology Products, Rockford, Ill. Non-limiting examples of these dyes are DyLight 675-B1, DyLight 675-B2, DyLight 675-B3, DyLight 675-B4, DyLight 679-05, DyLight 690-B1, DyLight 690-B2, DyLight 700-B1, DyLight 700-B2, DyLight 730-B1, DyLight 730-B2, DyLight 730-B3, DyLight 730-B4, DyLight 747-B1, DyLight 747-B2, DyLight 747-B3, DyLight 747-B4, DyLight 775-B2, DyLight 775-B3, DyLight 775-B4, DyLight 780-B1, DyLight 780-B2, DyLight 780-B3, DyLight 800, and DyLight 830-B2. Preferred near IR fluorophores are DyLight 780B and DyLight 800, which have the following structures:

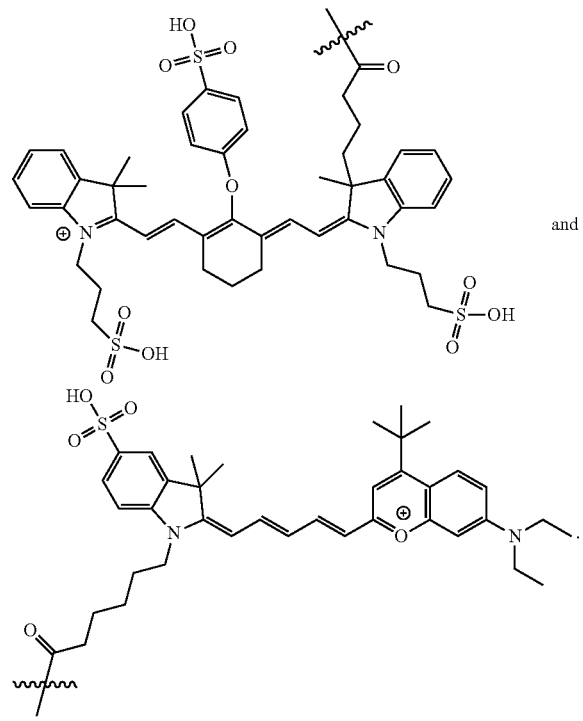

and

It should be understood that pharmaceutically acceptable salts of any of the above dyes are also considered suitable for these applications.

An example of a fluorescent label useful with visible wavelengths of light is fluorescein, which is widely used in immunofluorescence labeling. Fluorescein is a xanthene dye with an absorption maximum at 495 nanometers. A related fluorophore is Oregon green, a fluorinated derivative of fluorescein.

Other exemplary fluorescent labels suitable for use in the instant compounds are bora-diaza-indecene, rhodamine, and cyanine dyes. In particular, bora-diaza-indecene dyes are represented by 4,4-difluoro-4-bora-3a,4a-diaza-s-indacene, known as the BODIPY® dyes. Various derivatives of these dyes are known and are considered suitable for use as a detectable element in the compounds of the instant disclosure. See, e.g., Chen et al. (2000) *J. Org. Chem.* 65:2900-2906.

Rhodamine dyes are a class of dyes based on the rhodamine ring structure. Rhodamines include, inter alia, tetramethylrhodamine (TMR), a very common fluorophore for preparing protein conjugates, especially antibody and avidin conjugates, and carboxy tetramethyl-rhodamine (TAMRA), a dye commonly used for oligonucleotide labeling and automated nucleic acid sequencing. Rhodamines are established as natural supplements to fluorescein-based fluorophores, which offer longer wavelength emission maxima and thus open opportunities for multicolor labeling or staining.

Also included within the group of rhodamine dyes are the sulfonated rhodamine series of fluorophores known as Alexa Fluor dyes. The dramatic advances in modern fluorophore technology are exemplified by the Alexa Fluor dyes, which were introduced by Molecular Probes. These sulfonated rhodamine derivatives exhibit higher quantum yields for more intense fluorescence emission than spectrally similar probes, and have several additional improved features, including enhanced photostability, absorption spectra matched to common laser lines, pH insensitivity, and a high degree of water solubility.

The cyanine dyes correspond to a family of related dyes, Cy2, Cy3, Cy5, Cy7, and their derivatives, that are based on the partially saturated indole nitrogen heterocyclic nucleus with two aromatic units being connected via a polyalkene bridge of varying carbon number. These probes exhibit fluorescence excitation and emission profiles that are similar to many of the traditional dyes, such as fluorescein and tetramethylrhodamine, but with enhanced water solubility, photostability, and higher quantum yields. Most of the cyanine dyes are more environmentally stable than their traditional counterparts, rendering their fluorescence emission intensity less sensitive to pH and organic mounting media. In a manner similar to the Alexa Fluors, the excitation wavelengths of the Cy series of synthetic dyes are tuned specifically for use with common laser and arc-discharge sources, and the fluorescence emission can be detected with traditional filter combinations. The cyanine dyes are readily available as reactive dyes or fluorophores. The cyanine dyes generally have broader absorption spectra than members of the Alexa Fluor family, making them somewhat more versatile in the choice of laser excitation sources for confocal microscopy.

In specific embodiments, the detectable element of the instant compounds is the cyanine dye, Cy5.

In some embodiments, the fluorescent label used in the detectable element of the compounds of the instant invention may be a pH-dependent fluorophore. Such fluorescent labels display a fluorescence spectrum that depends on the pH of the label's environment, as would be understood by the skilled artisan, and may therefore be useful in reporting information about the environment of the label following reaction, for example information about the location of or type of protease labeled by the reactive compound. The pH-dependent fluorescence of various labels usefully included in the detectable element of the instant compounds is well known. See, e.g., *The Molecular Probes® Handbook—A Guide to Fluorescent Probes and Labeling Technologies*, which is hereby incorporated by reference in its entirety.

In some embodiments, it may be beneficial to include multiple detectable groups, e.g., fluorescent labels, radiolabels, chelated metals, and the like, within the detectable element of the compounds of the invention. Such multiple labeling can be achieved using routine coupling chemistry as would be understood by the skilled artisan.

The compounds of the instant specification typically also comprise a quencher group, Q. The term "quencher" refers to a chemical entity that modulates the emission of a fluorophore. In some cases, a quencher may itself be a fluorescent molecule that emits fluorescence at a characteristic wavelength distinct from the label whose fluorescence it is quenching. Thus, a fluorophore may act as a quencher when appropriately coupled to another dye and vice versa. In these situations, the increase in fluorescence from the acceptor molecule, which is of a different wavelength to that of the donor label, may separately report interactions of the labeled compound with its environment, such as, for example, the interior of a lysosome or other cellular compartment. In some cases, the quencher does not itself fluoresce (i.e., the quencher is a "dark acceptor"). Such quenchers include, for example, dabcyl, methyl red, the QSY diarylrhodamine dyes, and the like. In particular, dabcyl (4-dimethylamino-phenylazo)benzoic acid) is a common dark quencher used widely in many assays, such as "molecular beacons" for DNA detection. U.S. Pat. No. 5,989,823. Diazo dyes of the BHQ series, which are referred to as "Black Hole Quenchers", provide a broad range of absorption which overlaps well with the emission of many fluorophores. See PCT International Publication No. WO01/86001. The QSY series dyes from Molecular Probes is another example of dark quencher dyes that have been used extensively as quenching reagents in many bioassays. U.S. Pat. No. 6,399,392.

QSY 7 in particular is a nonfluorescent diarylrhodamine derivative. U.S. Patent Application Publication No. 2005/0014160. QSY21 is a nonfluorescent diarylrhodamine chromophore with strong absorption in the visible spectrum, and is an effective fluorescence quencher. Sulfo-QSY21 is a sulfonate version of QSY21 (see FIG. 1A). Fluorophore/quencher pairs are further illustrated in U.S. Patent Application Publication No. 2004/0241679.

Figure 6:
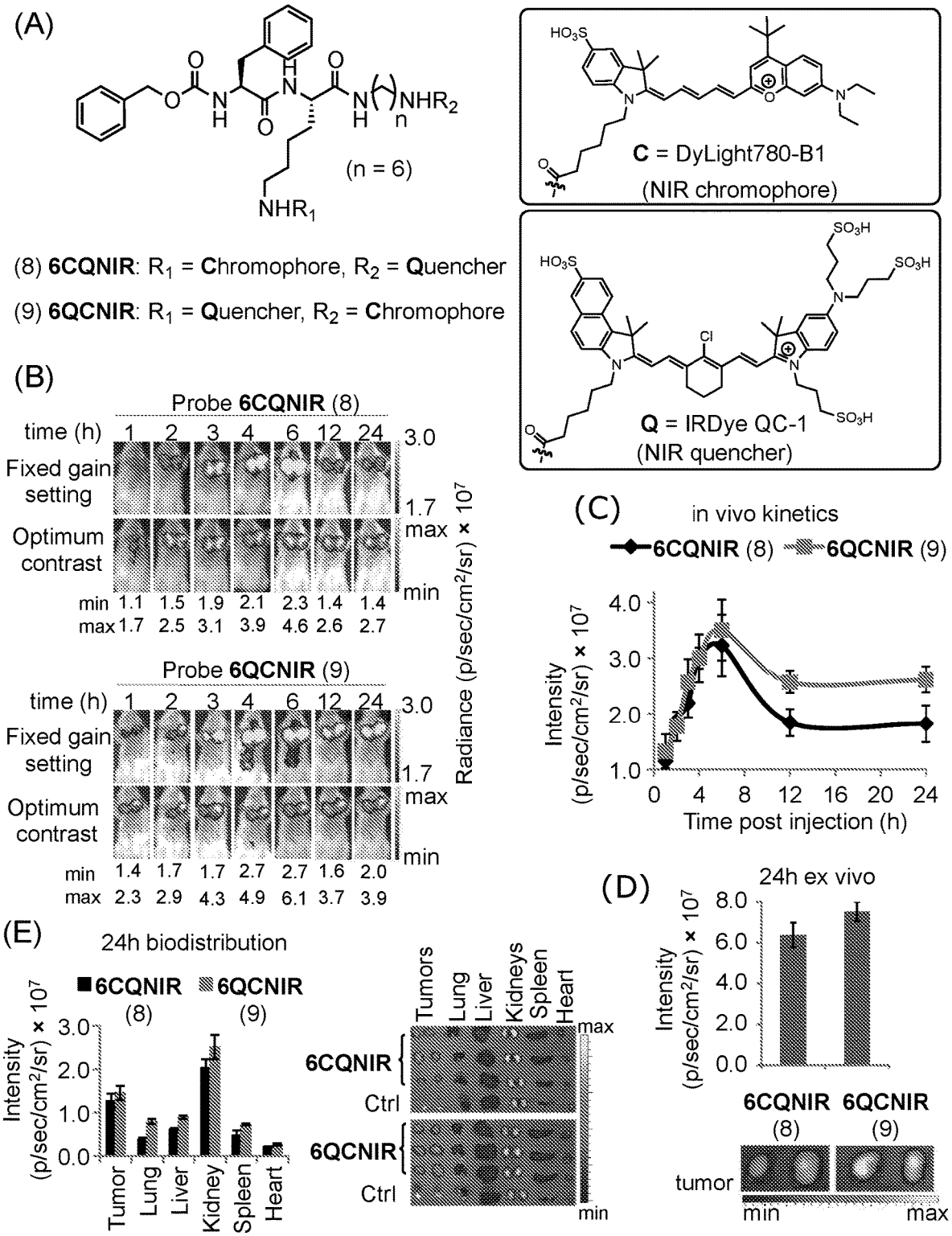
FIG. 6A-FIG. 6E. Evaluation of in vivo properties of optimized NIR probes. (A) Chemical structures of the near infrared quenched non-lysosomotropic substrate 6CQNIR (8) and lysosomotropic analog 6QCNIR (9). (B) Time course of non-invasive fluorescence imaging of tumor associated cysteine cathepsins in breast cancer mouse model using NIR probes. Images are shown for 1, 2, 3, 4, 6, 12 and 24 hour time points. The bottom panels represent the optimal fluorescence contrasts for each probe at the particular time point. (C) Quantification of tumor labeling kinetics of 6CQNIR and 6QCNIR over the 24 hour time course. N≥3 mice for each probe. Error bars represent the standard deviation on the mean. (D) Ex vivo images comparing tumors isolated from mice that received the two types of substrates. Isolation was at 4 hour and 24 hour time points. (E) Biodistribution of probes in various organs and tumors 24 hours after injection.

IRDye QC-1 (available from Li-Cor) is another example of a nonfluorescent dye that is suitable for use as a quencher in the instant compounds (see FIG. 6A). It efficiently quenches fluorescence from a wide range of fluorophores, including those ranging in wavelength from the visible region to the near-infrared.

In another aspect, the specification provides compounds having formula (II):

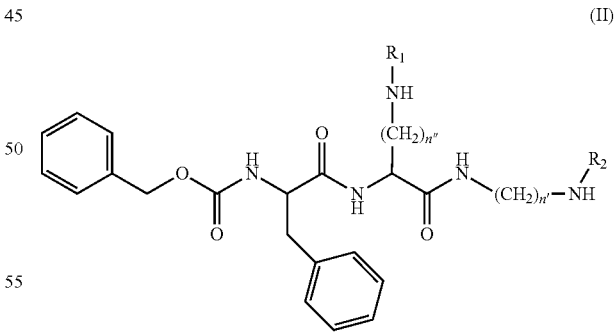

wherein n' and n" is each independently an integer from 2-8;
$R_1$ is a QSY quencher or QC-1; and
$R_2$ is a benzopyrillium or cyanine label.

In some embodiments of these compounds, n" is 4.
In some embodiments of these compounds, n' is 2, 4, or 6.

In specific embodiments, the compounds are selected from the group consisting of any of the following compounds:

23
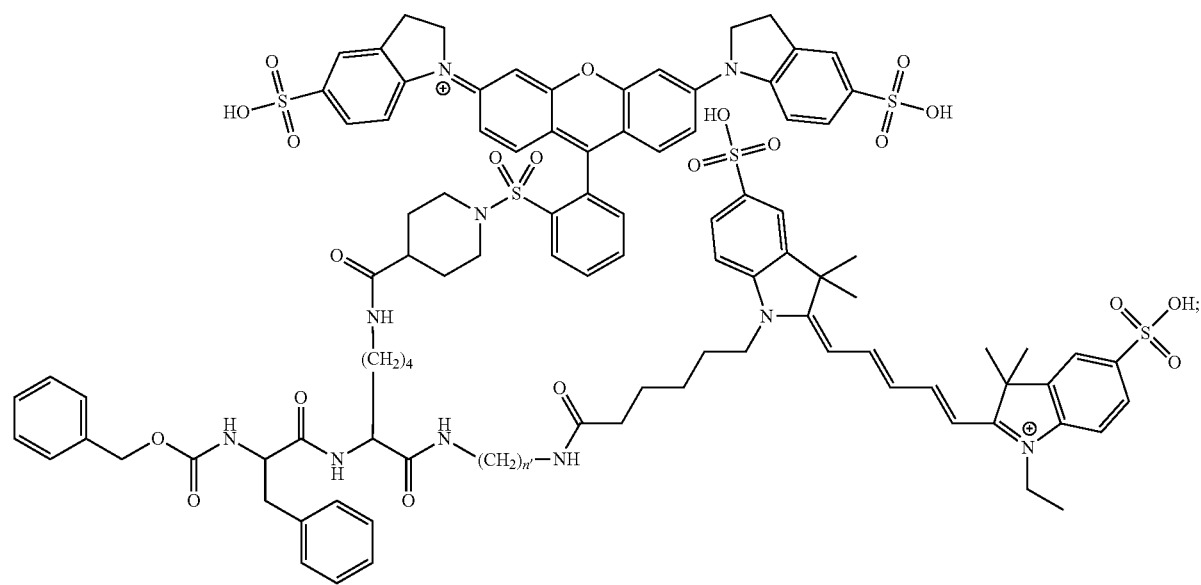
24
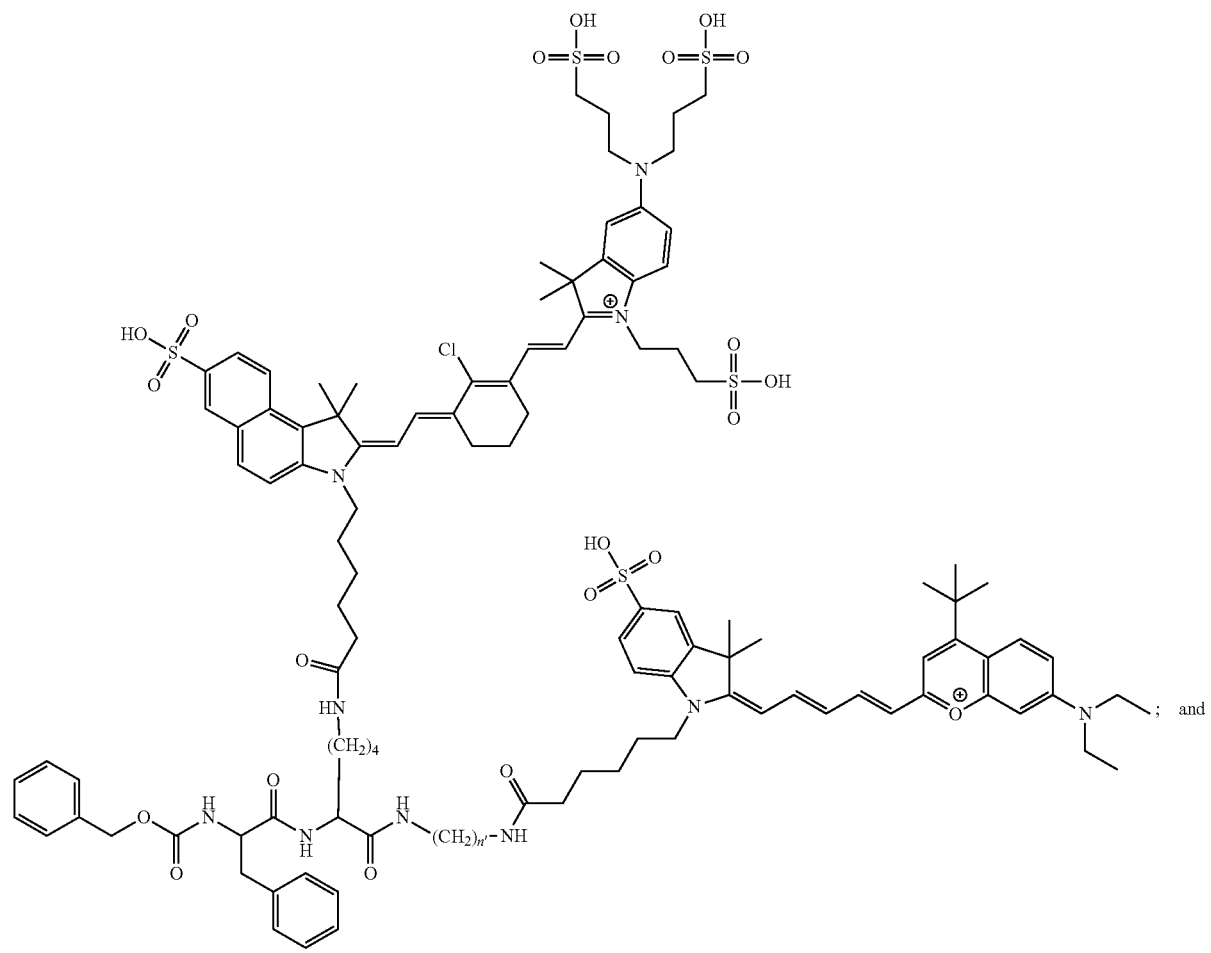

-continued

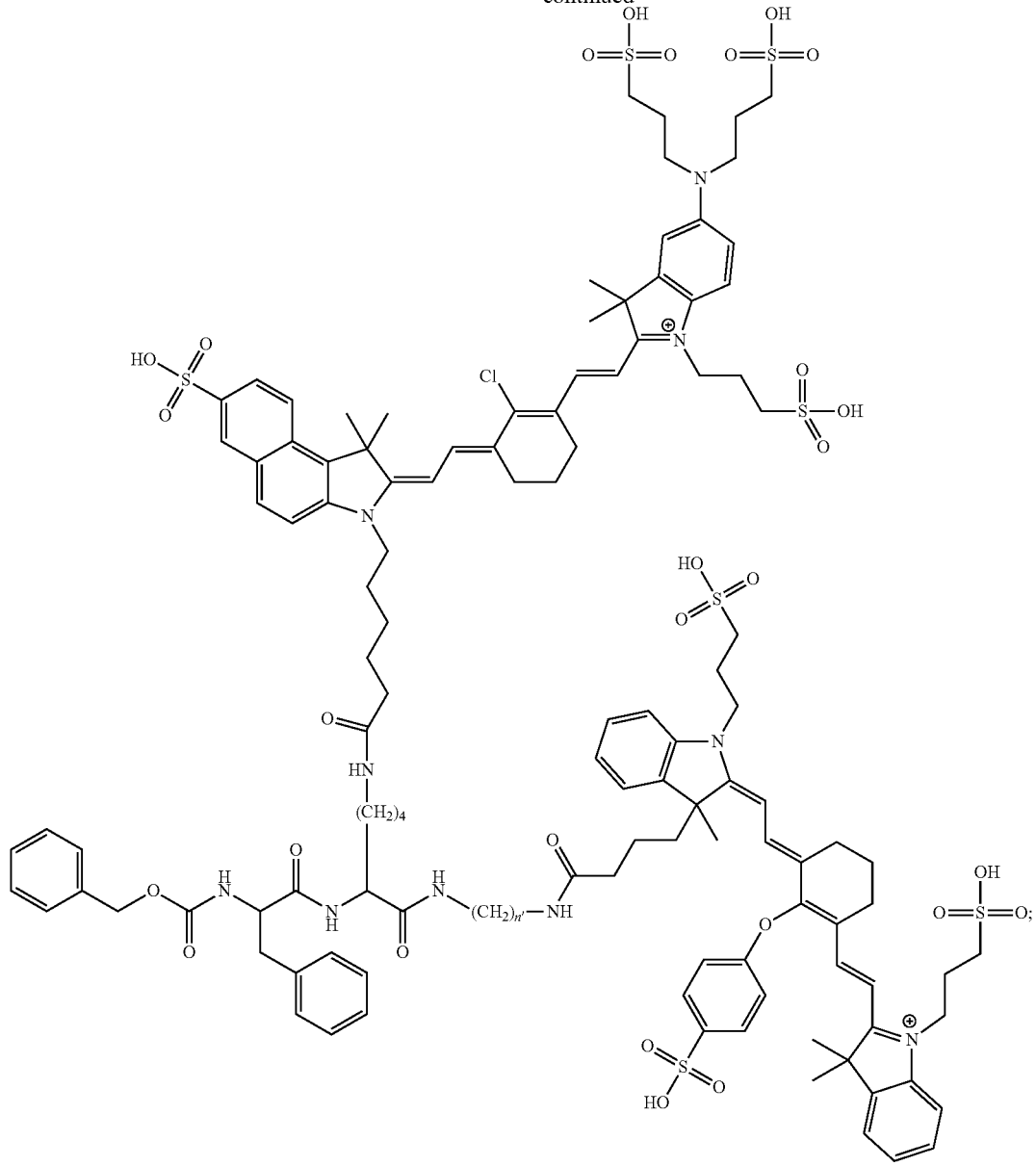

wherein n' is 2, 4, or 6; or pharmaceutically acceptable salts of these compounds.

According to another aspect, compound embodiments of the instant disclosure have the structure of formula (III):

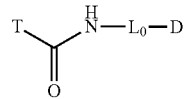

wherein

D is a detectable element;

$L_0$ is a linker; and

T is a protease targeting element, optionally comprising a quencher;

provided that $L_0$ does not comprise an ethoxyethoxy spacer.

The protease targeting element, T, in compounds of formula (III) is any suitable chemical structure that is capable of being recognized by a protease and catalytically hydrolyzed by the protease to release a lysosomotropic fragment, $D-L_0-NH_3^+$. Examples of such structures, including peptidic and non-peptidic protease targeting elements without limitation, are well known in the art of protease enzymology. In specific embodiments, the protease targeting element is a peptidic structure that contains no more than four amino acid residues or no more than three amino acid residues. In more specific embodiments, the protease targeting element is a peptidic structure that contains no more than two amino acid residues. For example, the compounds of formula (I), as shown above, comprise a protease targeting element that contains two amino acid residues. In specific embodiments, the protease targeting element is a structure that is selective for cleavage by cathepsin, and in particular by cathepsin L or cathepsin V.

According to some embodiments, the T group in compounds of formula (III) may be modified to increase the half-life of the subject compounds in vivo. In these embodiments, the T group may therefore comprise a polyethylene glycol moiety, a palmitate or other long-chain fatty acid moiety, an albumin binding protein, or the like, in order to stabilize the modified compounds.

In some embodiments of formula (III), $L_0$ does not comprise a polyethylene glycol group.

In some embodiments of formula (III), the protease targeting element is

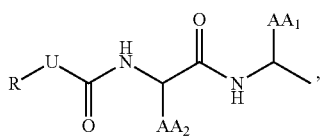

wherein
$AA_1$ and $AA_2$ is each independently an amino acid side chain,
U is O, N, or S, and
R is as defined above for compounds of formula (I).

In specific embodiments, $AA_1$ is a basic amino acid side chain and $AA_2$ is an aralkyl amino acid side chain, each optionally substituted with 1 to 3 A groups. In other specific embodiments, U is O. In still other specific embodiments, the R group is an aralkyl group such as, for example, a benzyl group.

In some embodiments of the above protease targeting element, $AA_1$ comprises a quencher. In these embodiments, $AA_1$ may have the structure $-L_1$-Q, wherein $L_1$ is a linker as defined above, and Q is a quencher.

In some of these embodiments, the $L_1$ group may be modified to increase the half-life of the subject compounds in vivo. In these embodiments, the $L_1$ group may therefore comprise a polyethylene glycol moiety, a palmitate or other long-chain fatty acid moiety, an albumin binding protein, or the like, in order to stabilize the modified compounds.

The detectable element, D, in compounds of formula (III) is any of the detectable groups described above. In specific embodiments, the detectable element comprises a fluorescent label or a radioactive substance, including a positron-emitting substance. In more specific embodiments, the detectable element comprises a fluorescent label, and the caspase targeting element, T, comprises a quencher.

In certain embodiments, the fluorescent label is a fluorescein, an Oregon green, a bora-diaza-indecene, a rhodamine, or a cyanine label. Specifically, the fluorescent label may be a cyanine label, such as Cy5. In certain other embodiments, the fluorescent label is a near infrared fluorescent label, such as a benzopyrillium or cyanine label. In specific embodiments, the benzopyrillium or cyanine label is a DyLight label, such as DyLight 780B dyes or DyLight 800.

In some embodiments of the compounds of formula (III), the detectable element comprises a radioactive substance.

The $L_0$ linker group in compounds of formula (III) may be any of the linkers described above.

Pharmaceutical Compositions

In another aspect, the instant invention provides pharmaceutical compositions comprising a compound of the invention and a pharmaceutically acceptable carrier. Such compositions are useful, for example, in the imaging of tissues in an animal and are further useful in assessing the activity of enzymes in the animal, for example, protease enzymes. In particular, for compounds of the invention that are protease substrates, and in particular cathepsin substrates, the pharmaceutical compositions may usefully serve as agents for the non-invasive optical imaging of cancer cells.

Pharmaceutically acceptable carriers are well known in the art and include, for example, aqueous solutions such as water or physiologically buffered saline or other solvents or vehicles such as glycols, glycerol, oils such as olive oil or injectable organic esters. In a specific embodiment, when such pharmaceutical compositions are for human administration, the aqueous solution is pyrogen free, or substantially pyrogen free. The excipients may be chosen, for example, to effect delayed release of an agent or to selectively target one or more cells, tissues or organs. The pharmaceutical composition may be in dosage unit form such as tablet, capsule, sprinkle capsule, granule, powder, syrup, suppository, injection or the like. The composition may also be present in a transdermal delivery system, e.g., a skin patch.

A pharmaceutically acceptable carrier may contain physiologically acceptable agents that act, for example, to stabilize or to increase the absorption of a compound of the instant invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition also may comprise a liposome or other polymer matrix, which may have incorporated therein, for example, a compound of the invention. Liposomes, for example, which consist of phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent, or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See *Remington: The Science and Practice of Pharmacy*, 20th ed. (Alfonso R. Gennaro ed.), 2000.

A pharmaceutical composition containing a compound of the instant invention may be administered to a subject by any of a number of routes of administration including, for example, orally (for example, drenches as in aqueous or non-aqueous solutions or suspensions, tablets, boluses, powders, granules, pastes for application to the tongue); sublingually; anally, rectally, or vaginally (for example, as a pessary, cream, or foam); parenterally (including intramuscularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). The compound may also be formulated for inhalation. In certain embodiments, a compound of the instant invention may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

Methods of Labeling Tissues and Visualizing Tumors

In another aspect, the disclosure provides methods of labeling a tissue in an animal, comprising the step of administering a composition of the invention to the animal.

In yet another aspect, the disclosure provides methods of visualizing a tumor in an animal, comprising the steps of administering a composition of the invention to the animal, and measuring a detectable signal generated in the animal from a reaction of the composition with a protease, specifically a cysteine protease, wherein the detectable signal is associated with a tumor in the animal.

In some of the method embodiments, the detectable signal is a fluorescent signal. In some embodiments, the fluorescent signal is generated at a tumor margin.

The administration of peptide imaging agents to an animal is well understood by those of ordinary skill in the art. In preferred embodiments, the agent is administered by injection, although any other suitable means of administration is considered within the scope of the invention.

The methods of the invention are directed at the labeling and visualization of a protease, in particular a cysteine protease, in an animal. Suitable animals include animals expressing cysteine proteases, particularly in tumor cells. In preferred embodiments, the animal is a mammal. In highly preferred embodiments, the animal is a human. In other preferred embodiments, the animal is a livestock animal or a pet.

In some embodiments, the methods of the invention comprise the step of measuring a detectable signal generated in the animal. Methods of measuring the detectable signal include, but are not limited to, imaging methods, for example fluorescent imaging methods. In some embodiments, the fluorescent imaging system is, for example, a Xenogen IVIS 100 system, an IVIS Spectrum system (PerkinElmer, Waltham, Mass.), or any other suitable non-invasive, in vivo fluorescence imaging system. In some embodiments, the detectable fluorescent signal is measured using a da Vinci Surgical System (Intuitive Surgical, Inc., Sunnyvale, Calif.). As described in further detail below, such systems may be used to implement the instant labeling and visualization methods in combination with intraoperative fluorescence-guided surgical techniques in patient tissues treated with the instant imaging agents.

In another aspect, the instant specification provides compounds for use in labeling a tissue in an animal. The compounds are described in detail above. These compounds, in combination with a pharmaceutically acceptable carrier, are administered to the animal in order to label the tissue. The compounds are also provided for use in visualizing a tumor in an animal. As above, the compounds, in combination with a pharmaceutically acceptable carrier, are administered to the animal, and a detectable signal generated in the animal from a reaction of the compound with a protease, specifically a cysteine protease, is measured in order to visualize the tumor.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Design and Synthesis of Quenched Fluorescence Substrates

The chemical structure of a recently-reported series of potent and selective ABPs (exemplified below as compound 1) was used as a starting point to design the quenched fluorescent substrate probes reported herein. See Verdoes et al. (2013) *J. Am. Chem. Soc.* 135:14726-30 and PCT International Publication No. WO2014/145257.

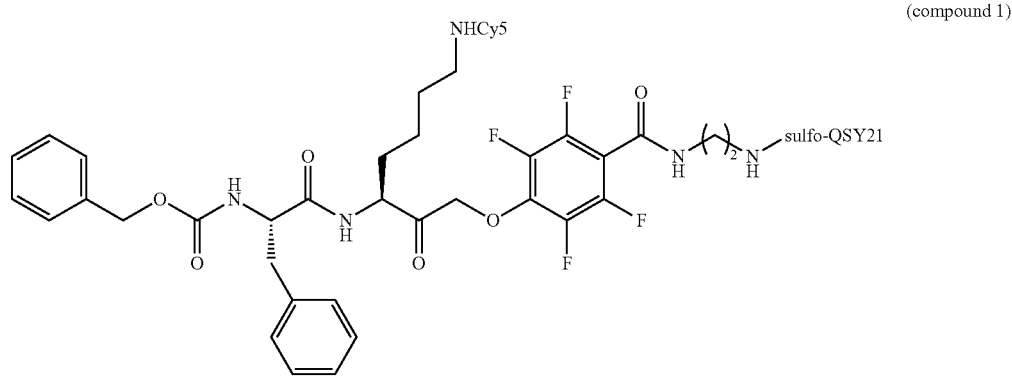

(compound 1)

As part of the design process, it was determined that the ability of the substrates to produce signal without inhibiting the target protease, coupled with an improved aqueous solubility would result in substrate analogs that activate faster and produce brighter signal in vivo compared to the original covalent probes. A cleavable amide bond was used in place of the irreversible thiol-reactive tetrafluoro phenoxymethyl ketone (PMK) electrophile (FIG. 1A). In order to select the optimum substrate for imaging cathepsin activity, a 6-membered library of quenched fluorescent substrate probes was designed by the introduction of two structural modifications. First, the lengths of the alkyl spacer between the substrate and the quencher were varied in order to measure the effect of the spacer length on the cleavage/unquenching efficiency of the probes by cathepsins. Three different spacer lengths were chosen, ranging from [$(CH_2)_n$], n=2, 4 and 6, representing substrates 2CQ (compound 2), 4CQ (compound 3), and 6CQ (compound 4). Second, the position of the Cy5 fluorophore was switched from the amine group of the lysine side chain to the terminal amine adjacent to the P1 amide bond to create substrates 2QC (compound 5), 4QC (compound 6), and 6QC (compound 7), respectively (FIG. 1A). The letters C and Q correspond to the fluorophore (Cy5) and quencher (QSY21-sulfo) components, respectively. Without intending to be bound by theory, it is believed that following enzymatic cleavage of the nQC probes in lysosomes, the free terminal amine on the Cy5 portion of the cleaved product becomes protonated due the acidic pH environment in the lysosomes. The resulting cationic Cy5 is thus retained in the lysosomal compartments due to the slow diffusion of cationic species across the membrane. The enhanced retention of the cationic fluorophore in the lysosomal compartments due to this latent lysosomotropic effect (LLE) in turn amplifies and sustains the duration of the fluorescence signal in the tumor site during non-invasive imaging (FIG. 1B).

Syntheses of all 6 substrate probes were accomplished by a combination of solid and solution phase chemistries as shown in Scheme 1, below. Fmoc solid phase chemistry was used to assemble the n-alkyl diamine, Boc-N-lysine, and Z-phenylalanine onto a 2-chlorotrityl chloride resin. Selective cleavage of the substrate from the resin using 1% trifluoroacetic acid (TFA) in dichloromethane generated the core structure of each substrate with the different lengths of alkyl spacers. After purification by reverse-phase preparative HPLC, the products were split into two parts. Sulfo-QSY21-NHS or Cy5-NHS was coupled to the free terminal amine of the separate halves in DMSO, followed by the removal of the Boc-protective group on the lysine in 50% TFA in DCM. The final quenched substrates were obtained by coupling either Cy5-NHS (for the nCQ substrates) or sulfo-QSY21-NHS (for the nQC substrates) onto the lysine side chain. After purification by HPLC, the probes were tested for activity against various recombinant cysteine cathepsins in vitro.

In Vitro Analyses of Quenched Fluorescent Substrates

The activity and selectivity of all 6 substrates were determined by monitoring the turnover curves of each internally quenched probe in the presence of various recombinant cysteine proteases, specifically cathepsins L, S, K, B, and V. Equal concentration (5 nM) of each enzyme was incubated with the different probes in 50 mM citrate buffer (pH=5.5, 5 mM DTT, 0.1% triton X, 0.5% CHAPS) at 37° C. The exact concentration of the various cathepsins used were confirmed by active site titration (Boucher et al. (2014) *Methods Mol. Biol.* 1133:3-39) using the covalent cysteine protease inhibitor ZFK-PMK and the commercial substrates Z-VVR-AMC for cathepsins S, L, B, and V, or Z-KR-AMC for cathepsin K. The rate of increase in Cy5 fluorescence (which is indicative of probe cleavage by cathepsins) was measured for each of the probes.

Figure 2:
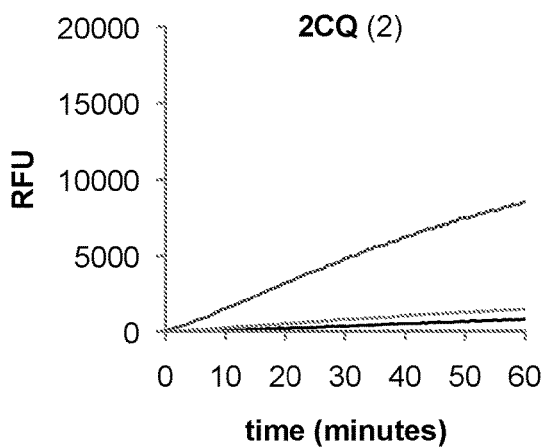
FIG. 2. Kinetic analysis of substrate cleavage by multiple cathepsins. Enzymatic turnover of quenched fluorescence nCQ and nQC substrates using recombinant cysteine cathepsins. The top trace in each panel corresponds to the activity with cathepsin L (Cat L). The next lower trace in each panel corresponds to the activity with cathepsin V (Cat V).
Figure 2:
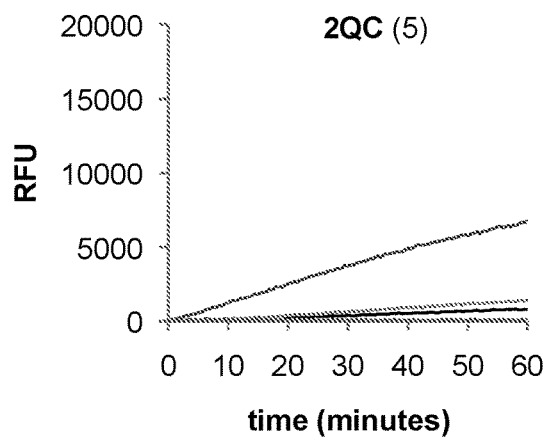
Figure 2:
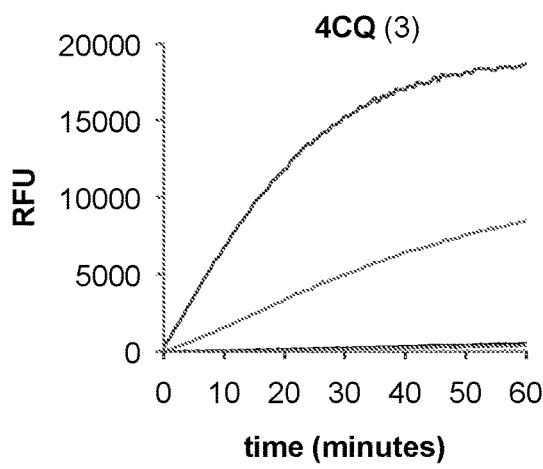
Figure 2:
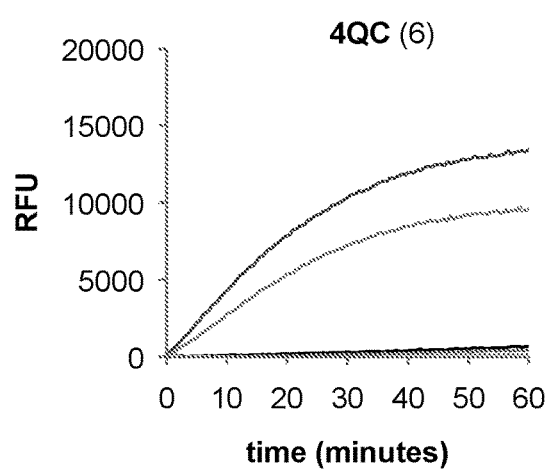
Figure 2:
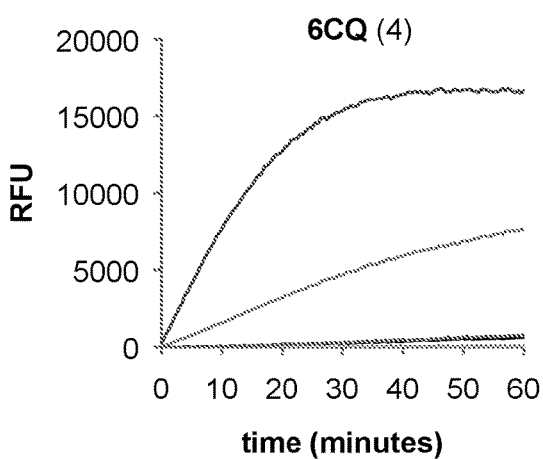
Figure 2:
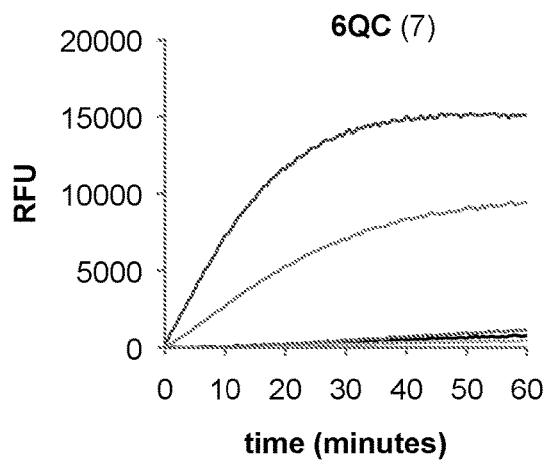

All of the quenched substrates (nQC and nCQ, n=2, 4, 6) were cleaved by cathepsins L, V, S and K, however, no increase in fluorescence was observed by cathepsin B under the conditions used (FIG. 2). Among the cathepsins tested, Cat L generated the highest increase in fluorescence with all probes, suggesting a strong selectivity of the library toward cysteine cathepsin L (FIG. 2, top trace in each panel). Interestingly, the cleavage of the substrates was not affected by the orientation of the fluorophore and quencher pair, since both nCQ and nQC probes were cleaved to the same extent by the various cathepsins (FIG. 2, left panels compared to right panels). In contrast, there appeared to be a strong correlation between the catalytic/cleavage efficiency ($K_{cat}/K_M$) by the enzymes and the length of the alkyl spacer adjacent to the p1 position of the substrate. For example, with respect to Cat L, a 4-fold increase in catalytic efficiency was observed between 2CQ and 6CQ, while a 6-fold increase was observed between 2QC and 6QC substrates (Table 1). This observation was consistent for Cat V, where an 8- and 4-fold increase in efficiency was observed between spacer lengths n equals to 2 and 6 respectively (Table 2). These differences in catalytic efficiencies entirely resulted from differences in the turnover numbers ($k_{cat}$), since the $K_m$ of all the substrates remained significantly the same for Cat L (Table 1). The higher enzymatic turnover of the substrates in vitro is particularly noteworthy, since higher turnover numbers may indicate faster activation of such probes in cells during non-invasive imaging.

TABLE 1

Enzyme kinetic parameters of the quenched substrates with recombinant cathepsin L. Data represent an average of three replicate experiments ± standard error on the mean.

| Probe | $K_m$ (µM) | $k_{cat}$ (s$^{-1}$) | $k_{cat}/K_m$ (M$^{-1}$s$^{-1}$) |
|---|---|---|---|
| (2) 2CQ | 6.4 ± 0.8 | 0.141 | 22,094 |
| (3) 4CQ | 4.6 ± 0.7 | 0.283 | 61,744 |
| (4) 6CQ | 5.4 ± 0.5 | 0.487 | 89,551 |
| (5) 2QC | 6.5 ± 1.5 | 0.095 | 14,687 |
| (6) 4QC | 8.6 ± 1.3 | 0.396 | 46,008 |
| (7) 6QC | 5.3 ± 0.8 | 0.458 | 86,763 |

TABLE 2

Enzyme kinetic parameters of the quenched substrates with recombinant cathepsin V. Data represent an average of three replicate experiments ± standard error on the mean.

| Probe | $K_m$ (µM) | $k_{cat}$ (s$^{-1}$) | $k_{cat}/K_m$ (M$^{-1}$s$^{-1}$) |
|---|---|---|---|
| (2) 2CQ | 5.0 ± 0.4 | 0.014 | 2,702 |
| (3) 4CQ | 3.4 ± 0.3 | 0.073 | 21,423 |
| (4) 6CQ | 6.8 ± 0.4 | 0.164 | 23,483 |
| (5) 2QC | 0.9 ± 0.1 | 0.008 | 7,951 |
| (6) 4QC | 4.8 ± 0.2 | 0.188 | 39,470 |
| (7) 6QC | 4.4 ± 0.2 | 0.150 | 34,104 |

Figure 3:
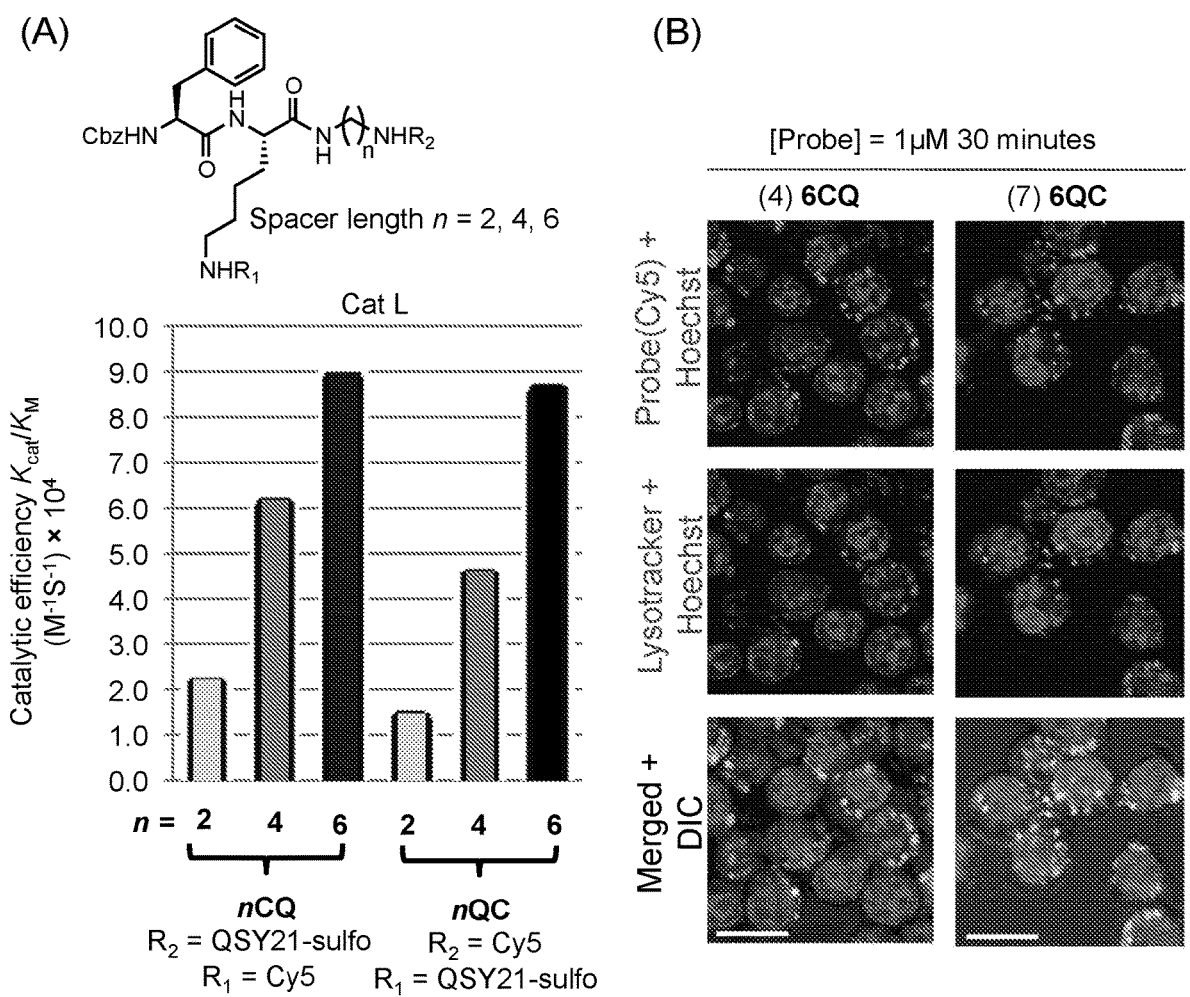
FIG. 3A-FIG. 3B. Comparison of LLE and non-LLE substrates in vitro. (A) Effect of varying space length on cleavage efficiency ($K_{cat}/K_M$) of quenched fluorescence nCQ and nQC substrates by recombinant cathepsin L. (B) Representative live cell fluorescence microscopy of RAW 264.7 cells incubated with 1 µM of quenched fluorescence substrates (6CQ and 6QC). Red (punctate cytosolic staining in top two panels) is Cy5 fluorescence of probes, green (punctate cytosolic staining in middle two panels) is lysotracker (a lysosome-selective stain), and blue (nuclear staining in top two and middle two panels) is Hoechst 33342. Scale bar represents 10 µm. Merged fluorescence (bottom two panels) shows the overlap of the Cy5 staining and lysotracker staining.

One hallmark of many forms of cancers is the increased infiltration of cathepsin rich immune cells such as macrophages to areas surrounding tumors. Shree et al. (2011) *Genes Dev.* 25:2465-79; Bell-McGuinn et al. (2007) *Cancer Res.* 67:7378-85. Hence, prior to utilizing the quenched substrates as possible reagents for non-invasive imaging of cysteine cathepsin activities, activation of the proteases in a macrophage derived cell line RAW264.7 was initially measured. Cells were incubated with the probes and then imaged by fluorescence microscopy. 1 µM each of the quenched substrates nCQ and nQC were incubated with RAW264.7 cells in DMEM with 10% FBS and for 30 minutes in a $CO_2$ atmosphere at 37° C. Cells were washed with PBS and stained with the lysosome selective marker Lysotracker Red and Hoechst 33342 nucleus stain, washed 3 times with PBS, and then suspended in PBS for live cell imaging. Strong Cy5 fluorescence probes was observed for each of the quenched substrate incubated with the cells, demonstrating that these probes are activated by cysteine proteases in this macrophage derived cell line (FIG. 3C). Labeling in the live cells was very selectively for acidic vesicles, as shown by the strong co-localization of the probe with the Lysotracker Red. The labeling morphology of the non-covalent substrates was similar to that of cells treated with the covalent label, compound 1, indicating a similar mode of entry into the cells.

Non-Invasive Optical Imaging of Tumors with Reversible Substrates

Figure 4:
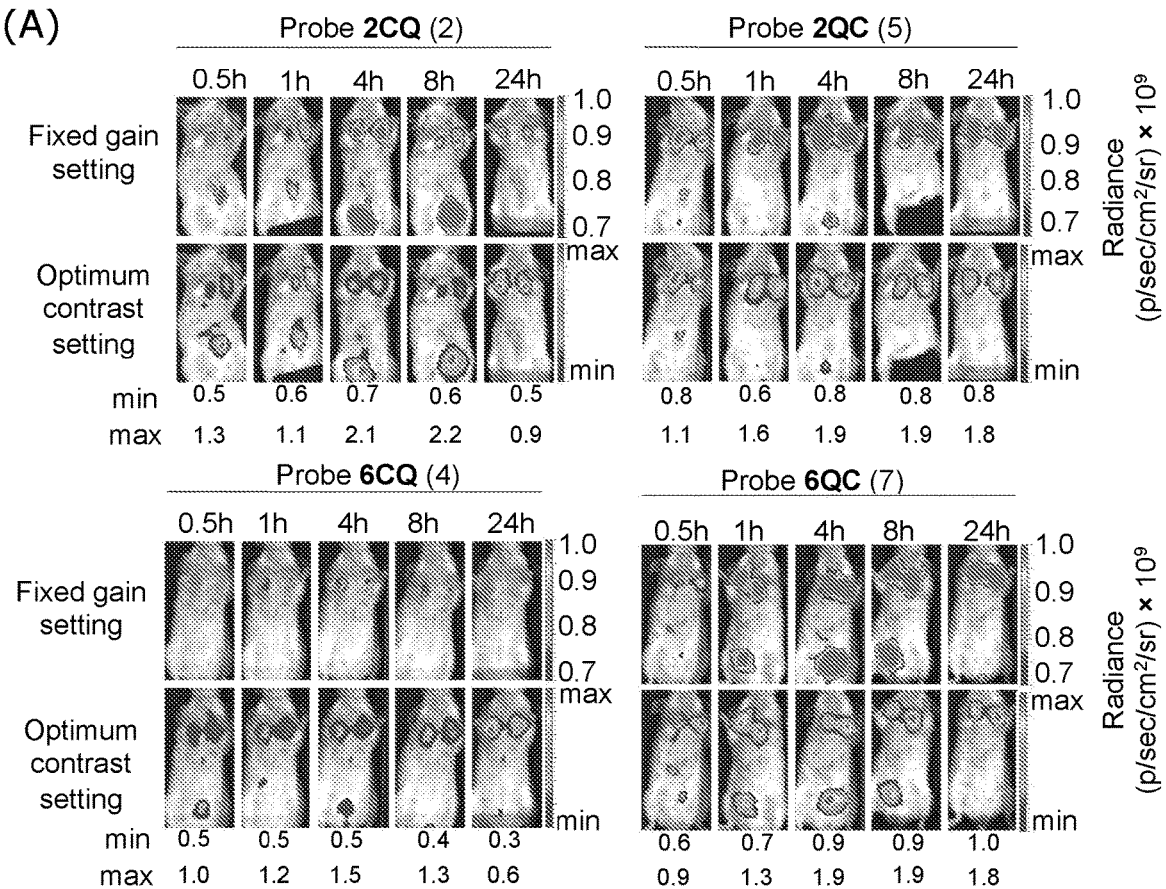
FIG. 4A-FIG. 4C. Validation of fluorescent substrates in the 4T1 breast cancer model. (A) Non-invasive time course fluorescence imaging of tumor associated cysteine cathepsins in mice injected with quenched fluorescence nCQ and nQC substrates (n=2, 6) and representative time point images at 0.5 1, 4, 8 and 24 hours post intravenous injection of probes. The bottom panels represent the optimal fluorescence contrasts for each probe at the particular time point. (B) Comparison of tumor labeling kinetics and pharmacokinetic properties of the non-lysosomotropic substrates, nCQ, and the lysosomotropic substrates, nQC, over a period of 24 hours. Error bars represent the standard deviation on the mean of N≥3 mice. Control mouse without probe was used to correct for auto-fluorescence. (C) Ex vivo tumor imaging at 4 hours and 24-hours post injection of the two types of substrate. Error bars represent the standard deviation on the mean of N≥3 mice.
Figure 4:
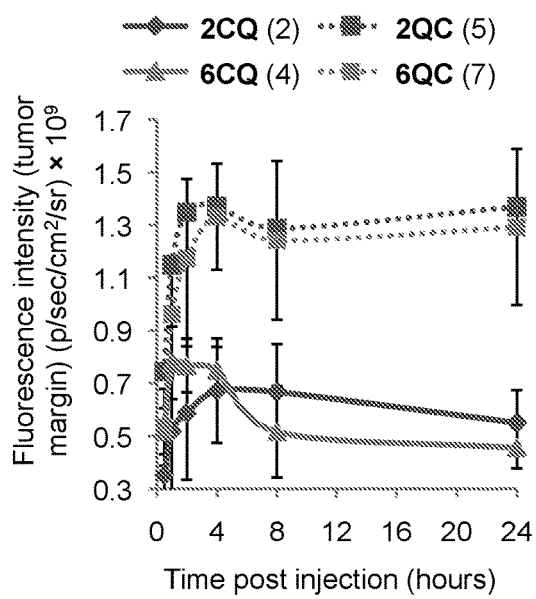
Figure 4:
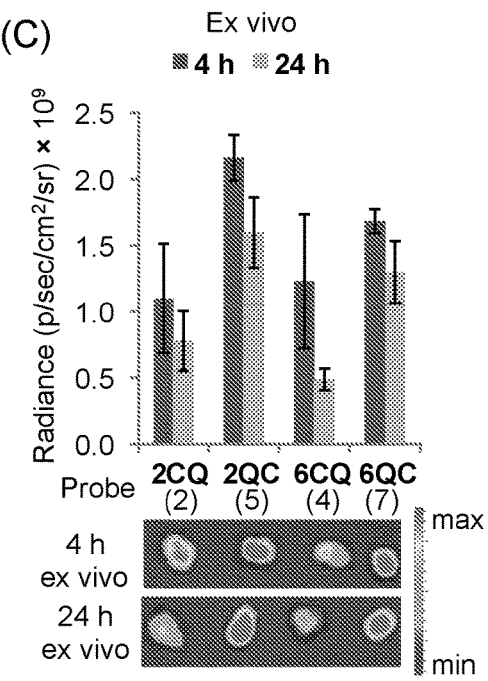

Having demonstrated the activities of the substrates in vitro and in cell-based assays, the substrates were next assessed in a syngeneic, orthotopic mouse model of breast cancer. In this model 4T1 cells are inoculated into the left number 1 and 10 mammary fat pad of mice to generate tumors. In order to determine the impact of the LLE, imaging signals of lysosomotropic probes 2QC (compound 5) and 6QC (compound 7) were directly compared to those of the non-lysosomotropic analogues 2CQ (compound 2) and 6CQ (compound 4). Substrates were administered to tumor-bearing mice intravenously, and mice were imaged at various time points following the administration. Rapid accumulation of Cy5 fluorescence from turnover of the quenched substrate probes was observed in and around the tumors in less than 30 minutes after administration, and sufficient contrast demarcating tumor from the surrounding normal tissues was observed within one hour (FIG. 4A). The intensity of the fluorescent signal reached a maximum at 4 hour after administration, followed by a decrease in the signal intensity (FIG. 4B). The overall absolute fluorescence intensity in the tumors was higher and brighter for mice injected with LLE substrates 2QC and 6QC compared to non-lysosomotropic substrates 2CQ and 6CQ. Furthermore, the intensity of the signal remained constant over a period of 24 hours in the tumors of mice administered with the LLE substrates, whereas the signals from the non-LLE substrates were almost completely cleared after 24 hours (FIGS. 4A and 4B). A similar trend was observed by ex vivo imaging of tumors excised from mice that had been euthanized after 4 hours and after 24 hours (FIG. 4C). These data demonstrate the value of the latent lysosomotropic effect in the design of low molecular weight reversibly binding contrast agents.

Figure 5:
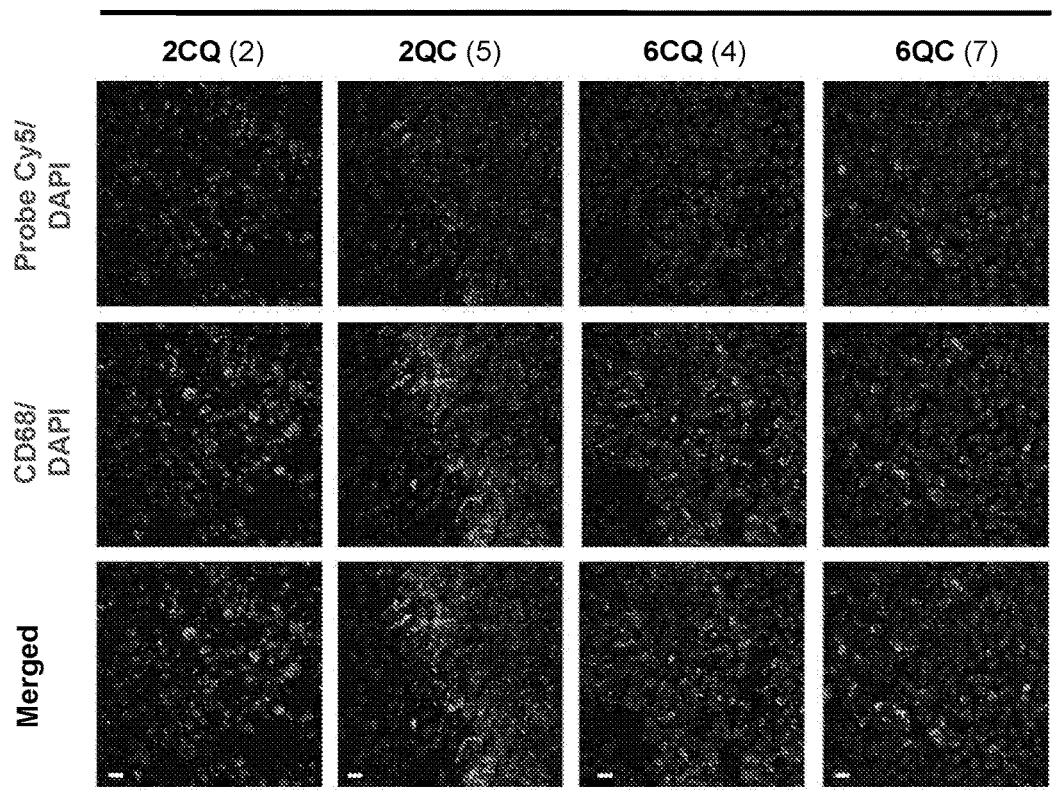
FIG. 5A-FIG. 5B. Confirmation of specific accumulation of the LLE substrate in tissues in vivo. (A) Histology on frozen sections of tumors excised from mice injected with substrates nCQ and nQC at the 24-hour endpoint. Cy5 fluorescence is shown in top panels (red staining; observed only in 2QC-treated and 6QC-treated animals), CD68 immunostaining for macrophages is shown in the middle panels (green staining; observed for all animals), DAPI (nuclear stain) is shown in top and middle panels (blue staining). Bottom row of panels shows the merged fluorescence. (B) Biodistribution of probes in various organs 4 hours and 24 hours after intravenous administration. Error bars represent the standard deviation on the mean of N≥3 for each time point.
Figure 5:
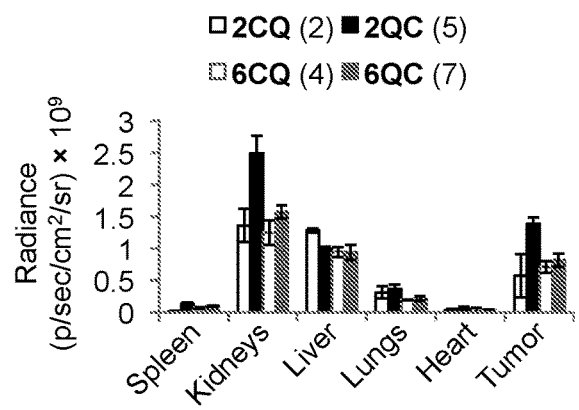
Figure 5:
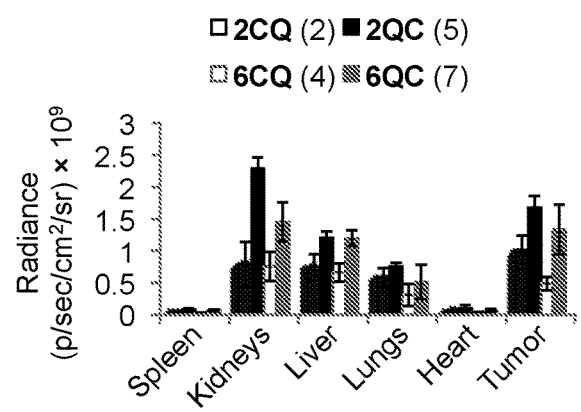

In order to determine which populations of cells are responsible for activating the quenched substrate probes in vivo, immunofluorescence staining on frozen sliced sections of tumors isolated from mice injected with each substrate was performed using a macrophage-selective marker CD68. The Cy5 signal of the substrate co-localized to only CD68-positive cells (macrophages), with no signals observed in the 4T1 tumor cell (FIG. 5A). Moreover, Cy5 fluorescence was only observed in tissues from mice that received nQC substrates and not in tissues from mice treated with nCQ substrates (FIG. 5A). These results further validate the utility of LLE as a strategy to enhance probe retention in tumors.

Application of Probes in FGS Using the Da Vinci Surgical System

The Da Vinci surgical system is a robotic surgical system manufactured by Intuitive Surgical Inc. that is currently used in clinics all over the world for laparoscopic surgery. Surgical procedures using this system are currently performed under white light illumination, however, which does not provide sufficient contrast to demarcate the margins of tumors from the surrounding normal tissues. The development of a tumor-targeted contrast agent that is also compatible with the existing Da Vinci system is therefore of great value, and should result in markedly improved treatment outcomes in fluorescence-guided surgery (FGS).

The optimized substrate probes described above have therefore been tested in a clinically relevant model systems of FGS. In order achieve these results, reversible probes 6CQNIR (compound 8) and the lysosomotropic analog of this substrate, 6QCNIR (compound 9) has therefore been synthesized. In these compounds, the Cy5 chromophore was strategically substituted with a similar molecular weight near infrared (NIR) DyLight 780-B1 fluorophore. The compound with a linker having n=6 was chosen based on the optimal turnover numbers by cathepsins in vitro. The QSY21-sulfo quencher was also substituted with IRDye QC-1, which is a dark NIR quencher (FIG. 6A). In addition to being detectable on the camera system of the da Vinci robot, the emission wavelength of the NIR dye (absorption/emission maxima of 783/799 nm) falls within a window with low overall background and will therefore enhance tissue penetration and improve signal to background ratio during imaging. Richards-Kortum and Sevick-Muraca (1996) *Annu. Rev. Phys. Chem.* 47:555-606. The NIR probes were first analyzed as contrast agents in the 4T1 breast cancer model described above, using the IVIS-spectrum imaging system. Following systemic administration of the contrast agents, mice were imaged non-invasively every hour for 4 hours, and then at 6, 8, 12 and 24 hours post injection of the substrate. A rapid accumulation of the probe signal was observed in the implanted breast tumors. Specifically, substantial contrast that demarcated the tumor margin from healthy surrounding tissues was observed as early as 1-hour post injection of both probes (FIG. 6B). The intensity of the fluorescence signal in the tumors increased rapidly in mice injected with both types of probes, and it eventually peaked between 4 to 6 hours. This time-point may signify an optimum window for imaging tumors following systemic administration of this class of non-covalent quenched fluorescent probes. Similar to the initial probes, the near infrared analogs showed a lysosomal trapping effect as evidence by the slower clearance rate and brighter signal in tumors of mice injected with the LLE substrate 6QCNIR relative to the non-LLE substrate (FIG. 6C). Between 1 and 4 hours, both substrates showed similar initial intensity, indicating that the activation rates of both substrates by cathepsins are equal.

Figure 7:
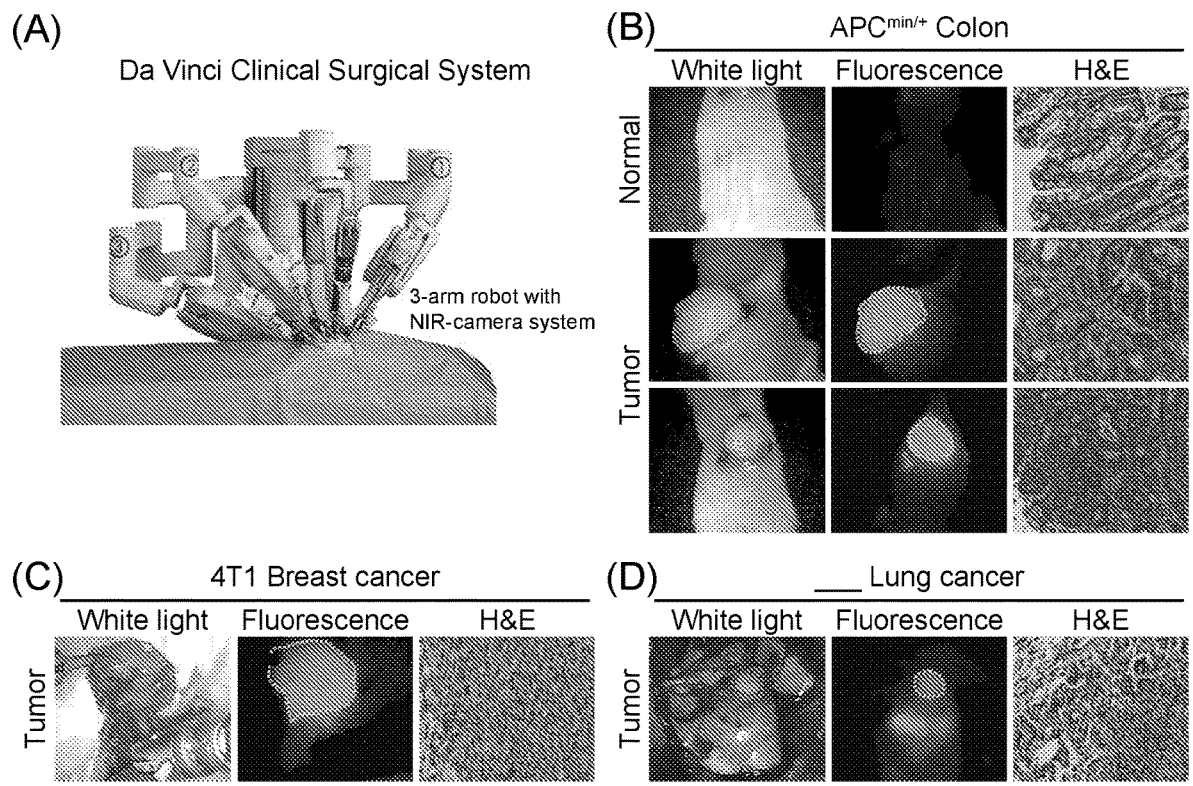
FIG. 7A-FIG. 7D. Intraoperative fluorescence image guided detection and resection of colorectal, breast and lung adenocarcinomas, employing the clinical da Vinci surgical instrument in conjunction with a designed cathepsin probe. (A) Graphical illustration of the da Vinci surgical robot system equipped with a NIR camera. (B) Detection of polyps in the colon of colorectal cancer $APC^{min+}$ mouse model 6 hours after intravenous administration of LLE protease targeted contrast agent, 6QCNIR (9). Images were obtained from screenshots of the real time intraoperative imaging of the splayed colon. The panels show representative images of polyps detected in the colon of the same mouse illuminated by white light (left), fluorescence (center) and H&E stain (right) of the resected tumor. (C) Detection and fluorescent image guided surgical removal of mouse breast tumors (4T1) using the clinical instrument and the contrast agent 6QCNIR. The images compare white light illumination of tumor and tumor bed (left), fluorescence (center), and confirmation of malignancy of the tumor by H&E stain (right). (D) Application of the probes in the detection and resection of mouse lung cancer and correlation of cancer with histology.

With the positive results using the small animal imaging system, image-guided resection studies using the da Vinci surgical system were next performed. This robotic surgery system (FIG. 7A) can be used to perform minimally-invasive laparoscopic surgical procedures. The system is also equipped with a NIR camera that can be used in addition to the white light imaging system to visualize contrast agents carrying NIR signals. It was thus possible to perform tumor resection studies in multiple models of cancer. Surgical resections on models of colon cancer (APC mice; FIG. 7B, FIG. 7C) were chosen, as well as breast cancer (4T1 transplant model; FIG. 7D, FIG. 7E) and a model of metastatic lung cancer (FIG. 7F). For each surgery, the da Vinci robot was used to perform a resection of positive probe signals. Tissues were also removed from the animals in order to performed histological analysis and thus to confirm the presence of cancer cells in the substrate-positive tissues.

Overall these data confirmed that the NIR fluorescent substrate probes were able to highlight tumors in all three models of cancer. Furthermore, the existing da Vinci robot system could be used to identify cancer lesions and remove them for further analysis.

Figure 8:
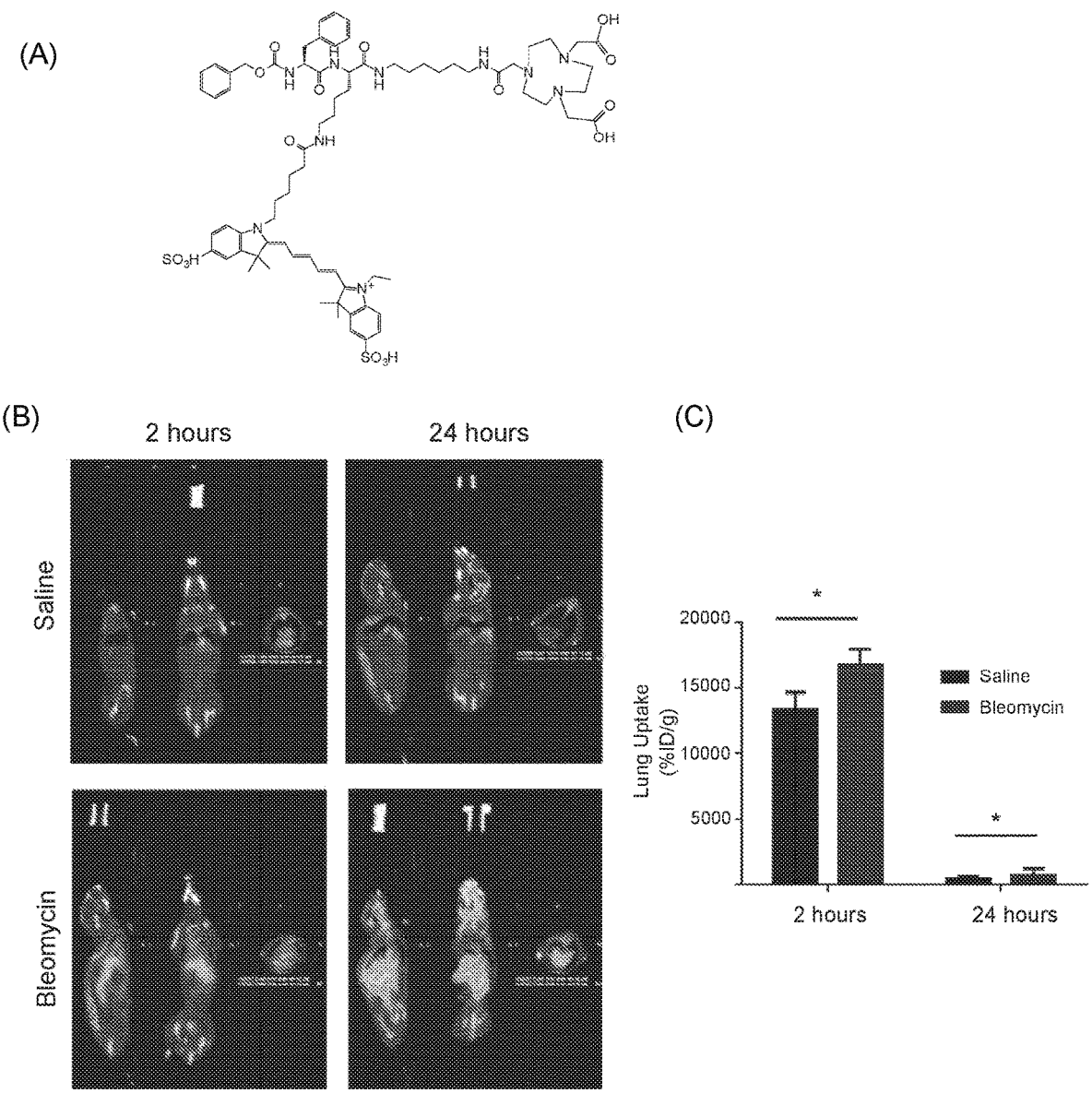
FIG. 8A-FIG. 8C. Design and validation of PET substrate probe for imaging cathepsins. (A) Structures of the substrate probe LO263. (B) Non-invasive PET/CT scans of mice treated with saline or bleomycin at Day 7 at 2 hours and 24 hours of imagining. Coronal (left), transaxial (top right) and sagittal (bottom right) images are shown for representative mice from saline or bleomycin-treated groups at the indicated time points. (C) Quantification of PET/CT intensity from lungs of all mice at Day 7 in the different treatment groups. Error bars indicate mean±SEM., Day 7 (saline n=4; bleomycin n=4. *p<0.05 by t-test).

FIG. 8A-FIG. 8C show the structure of a cathepsin probe containing a chelator in the leaving group and the use of the PET substrate probe for imaging cathepsin activity in animals.

Methods

General

All resins and reagents were purchased from commercial suppliers and used without further purifications. Water used for reactions and aqueous workup was glass-distilled from a deionized water feed. Reagent grade solvents were used for all non-aqueous extractions. All water-sensitive reactions were performed in anhydrous solvents under positive pressure of argon. Reactions were analyzed by LC-MS using an API 150EX single-quadrupole mass spectrometer (Applied Biosystems). Synthesized compounds were purified via Reverse-phase HPLC with an AKTA explorer 100 (Amersham Pharmacia Biotech) using $C_{18}$ columns. Compounds were eluted with and a gradient of doubly distilled water and acetonitrile containing 1% trifluoracetic acid as solvents. NMR spectra were recorded on a Varian 400 MHz (400/100), Varian 500 MHz (500/125) equipped with a pulsed field gradient accessory. $^1$H NMR spectra were recorded at 25° C. on either a Bruker Avance 400 (400 MHz) or Bruker Avance 500 (500 MHz) instrument and processed using MestReNova NMR processing software. Chemical shifts (δ) are reported in parts per million (ppm) downfield from tetramethylsilane and referenced to the residual protium signal in the NMR solvents (CDCl$_3$, δ=7.25). Data are reported as follows: chemical shift, multiplicity (s=singlet, d=doublet, t=triplet, m=multiplet and q=quartet), coupling constant (J) in Hertz (Hz) and integration. Cells were cultured in Dulbecco's modified Eagle's medium (DMEM (GIBCO Cat #11995)), supplemented with 10% FBS and 1% pen-strep.

Compound Synthesis

Scheme 1 summarizes the synthesis of the initial series of fluorescent substrates used in these studies.

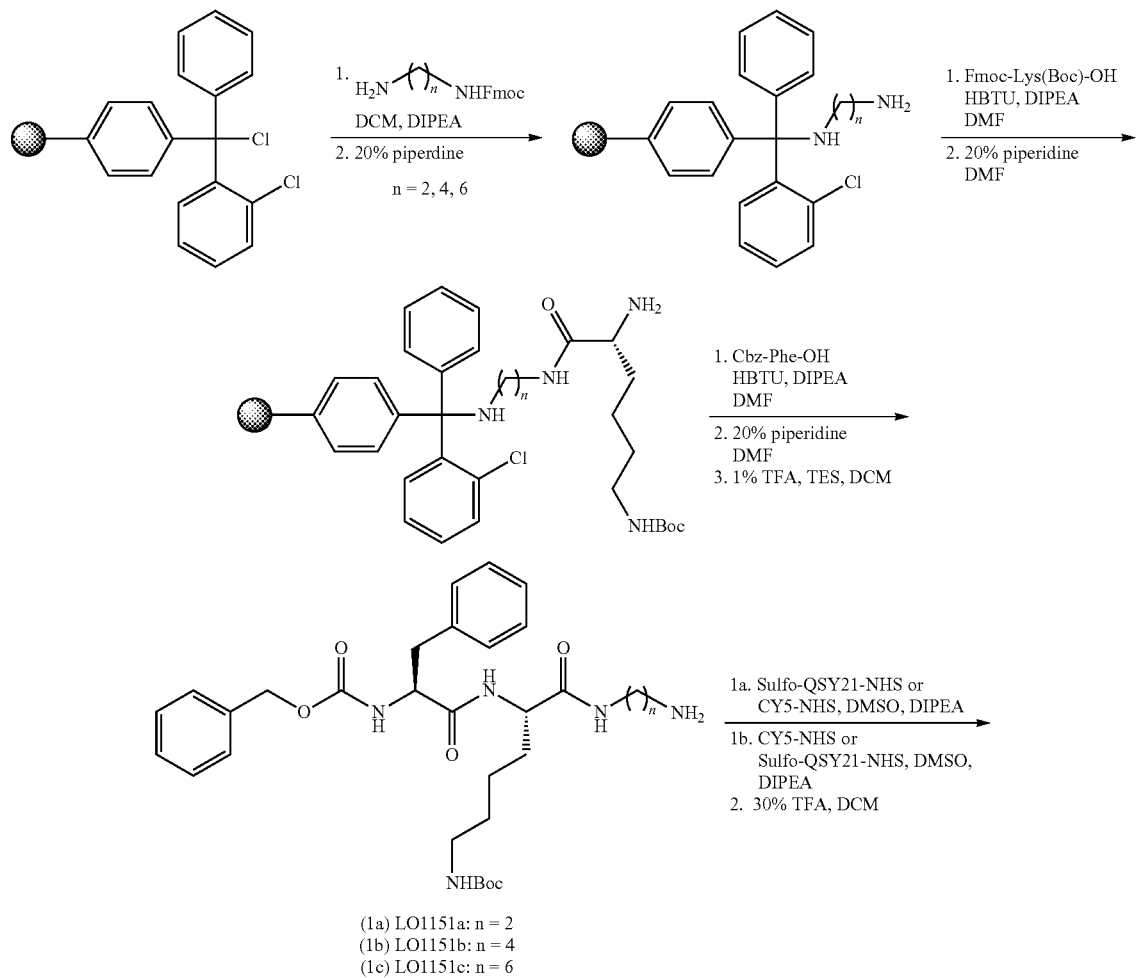

Scheme 1. Synthesis of a 6-member library of non-covalent quenched fluorescent activity based substrates.

(1a) LO1151a: n = 2
(1b) LO1151b: n = 4
(1c) LO1151c: n = 6

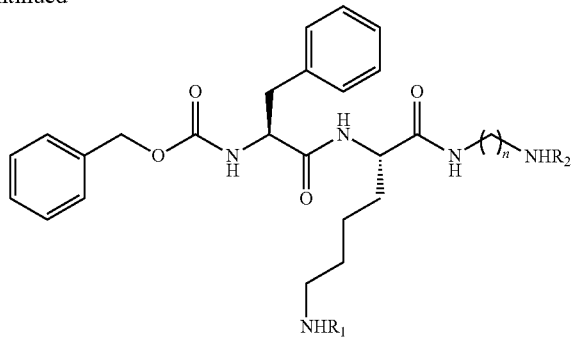

6-member library of non-covalent quenched fluorescence activity based probes non-lysosomotropic probes: LOnCQ
(2) LO2CQ: $R_1$ = Cy5, $R_2$ = QSY21-sulfo, n =2
(3) LO4CQ: $R_1$ = Cy5, $R_2$ = QSY21-sulfo, n =4
(4) LO6CQ: $R_1$ = Cy5, $R_2$ = QSY21-sulfo, n = 6
Latent lysosomotropic effect probes: LOnQC
(5) LO2QC: $R_1$ = QSY21-sulfo, $R_2$ = Cy5, n =2
(6) LO4QC: $R_1$ = QSY21-sulfo, $R_2$ = Cy5, n =4
(7) LO6QC: $R_1$ = QSY21-sulfo, $R_2$ = Cy5, n = 6

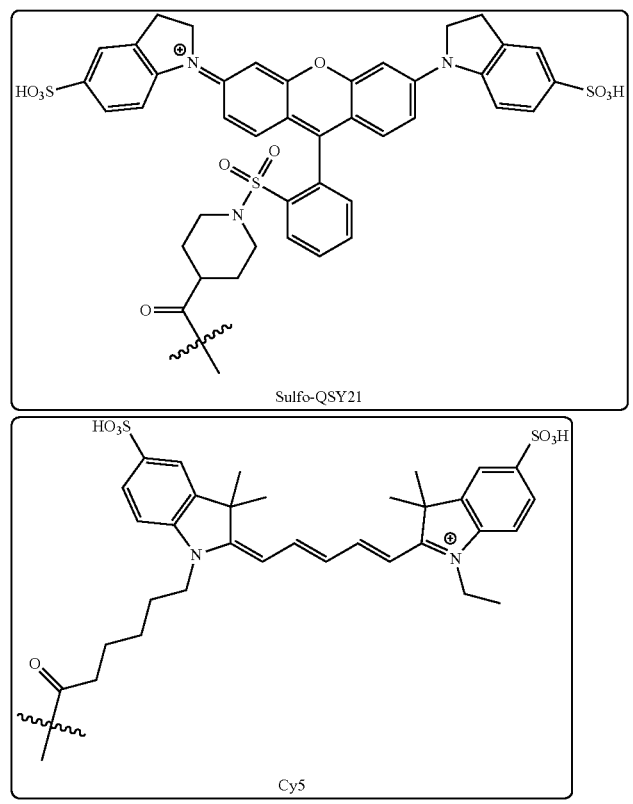

Intermediates 1a, 1b, and 1c.

0.5 g of 2-chlorortrityl chloride resin (0.84 mmol/g loading) was weighed into three separate solid phase reaction vessels. The reaction vessels were labeled from a to c. Dichloromethane (DCM) was added to suspend the resins and then reaction was agitated for 15 minutes using a laboratory shaker. After washing 2 times with DCM, mono-Fmoc-1,3-ethanediamine (0.35 g, 1.26 mmol), mono-Fmoc-1,4-butanediamine (0.39 g, 1.26 mmol), and mono-Fmoc1,6-hexanediamine (0.43 g, 1.26 mmol) in 3 mL of DCM were added to the resin in vessels a, b, and c respectively. Diisopropylthylamine (DIPEA, 3 eq) was then added to each and the reaction was agitated for a period of 30 minutes at room temperature. The resin was then washed with DCM and then suspended in methanol for 10 minutes in order to deactivate unreacted trityl-chloride. Fmoc deprotection was achieved by suspending the resin in a solution of 20% piperidine in DMF for duration of 1 hour, followed by 3 times wash with DCM and DMF respectively. Next, the first amino acid Fmoc-Lys(Boc)-OH (0.58 g, 1.26 mmol) was coupled to the resin using HBTU (0.48 g, 1.26 mmol) and DIPEA (0.17 g, 1.26 mmol) in 3 mL DMF and rotating the mixture for 2 h. Following a wash cycle, Fmoc deprotection was accomplished using 5 mL of 20% piperidine in DMF for 1 hour, followed again by the wash cycle. The remaining amino acid Cbz-Phe-OH was similarly coupled to the peptide on the resin. The resin was then treated with a solution 1% trifluoroactic acid in DCM to selectively cleave the peptide (with a resulting Boc-protected lysine) from the resin. The solvent was removed from each cleaved product by co-evaporating with toluene, resulting in the intermediate substrates 1a, 1b, and 1c, respectively (Scheme 1). Each product was then further purified by reversed-phase preparative HPLC to afford the final peptides in greater than 95% purity.

Substrates 2CQ, 4CQ, and 6CQ (Compounds 2, 3, and 4)

In a separate 1 mL eppendorf tubes, intermediates 1a (2.0 mg, μmol), 1b (2.0 mg, μmol) and 1c (2.0 mg, μmol) was dissolved in 100 μL of DMSO. DIPEA (3 μL, μmol) was added followed by QSY21-sulfo-NHS (1.2, mmol). The reaction was stirred for 1 hour at room temperature followed by purification of the product by HPLC. The solvent was removed by rotary evaporation after which the Boc-protection on the lysine was removed by treatment with 30% TFA in DCM for 30 minutes. Following removal of the solvent, the product was lyophilized and then reacted with Cy5-NHS in DMSO and 3 equivalent of DIPEA (Scheme 1). The final products were each purified by reverse-phase HPLC to yield the non-lysosomotropic quenched fluorescence substrates nCQ, where n=2, 4, and 6, respectively.

Substrates 2QC, 4QC, and 6QC (Compounds 5, 6, and 7)

In a separate 1 mL eppendorf tubes, intermediates 1a (2.0 mg, μmol), 1b (2.0 mg, μmol) and 1c (2.0 mg, μmol) were dissolved in 100 μL of DMSO. DIPEA (3 μL, μmol) was added followed by Cy5-NHS (1.2, mmol). The reaction was stirred for 1 hour at room temperature followed by purification of the product by HPLC. The solvent was removed by rotary evaporation after which the Boc-protection on the lysine was removed by treatment with 30% TFA in DCM for 30 minutes. Following removal of the solvent, the products were lyophilized and then reacted with QSY21-sulfo-NHS in DMSO and 3 equivalent of DIPEA (Scheme 1). The final products were each purified by reverse-phase HPLC to yield the latent lysosomotropic effect quenched fluorescence substrates nQC, where n=, 2, 4, and 6, respectively.

Scheme 2. Synthesis of near infrared non-covalent quenched fluorescent activity based probe compatible with the da Vinci surgical robot

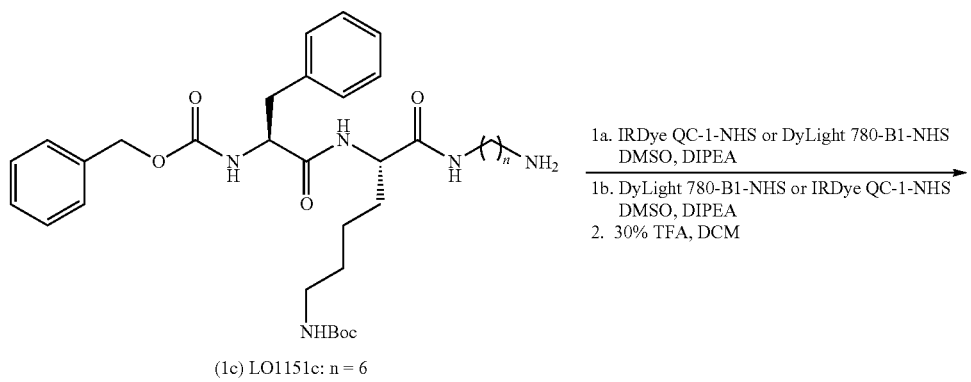

(1c) LO1151c: n = 6

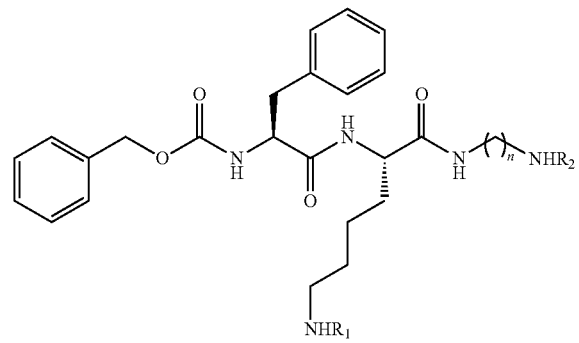

(8) LO6CQNIR: $R_1$ = DyLight 780-B1, $R_2$ = IRDye QC-1, n = 6
(9) LO6QCNIR: $R_1$ = IRDye QC-1, $R_2$ = DyLight 780-B1, n = 6

-continued

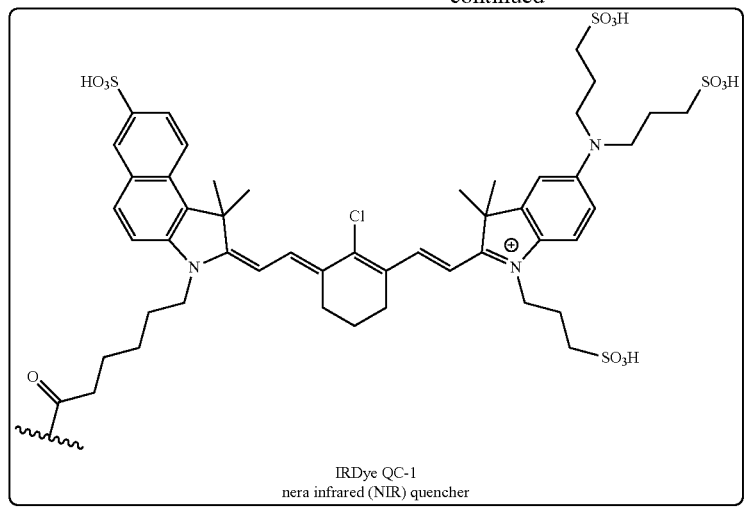

IRDye QC-1
nera infrared (NIR) quencher

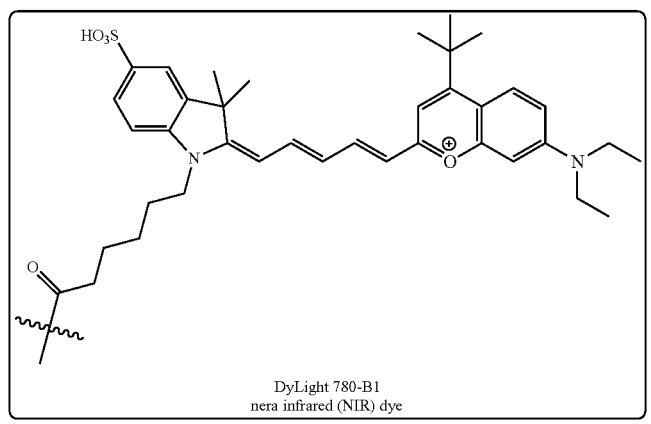

DyLight 780-B1
nera infrared (NIR) dye

Radiolabeling

Briefly, $^{64}$Cu-LO263 was prepared by incubation of 10 μL LO263 (10 mM) (FIG. 8A) in 90 μL sodium acetate buffer (0.1M, pH 5.5) with 4 mCi of $^{64}$CuCl$_2$ in 100 μL sodium acetate buffer (0.1M, pH 5.5) at 37° C. for 1 hour. After cooling to room temperature, the reaction mixture was analyzed by RP-HPLC. The $^{64}$Cu-LO263 was then purified by RP-HPLC with the mobile phase starting from 95% solvent A (di-water with 0.1% TFA) and 5% solvent B (acetonitrile with 0.1% TFA) for 3 min to 5% solvent A and 95% solvent B at 23 min. The eluted fractions containing $^{64}$Cu-LO263 (retention time 18.9 min) were then collected and dried using a rotary evaporator. The radiolabeling yield was 90% (calculated from the HPLC). The radiochemical purity, defined as the ratio of the main product peak to other peaks, was determined by radio-HPLC to be >95%, and the specific activity of the probe was determined to be 3-4 Ci/mmol. The $^{64}$Cu-LO263 was then reconstituted in 0.9% saline and passed through a 0.22 μm Millipore filter into a sterile vial for animal PET/CT imaging.

PET In Vivo Imaging

Mice were intravenous injected with 100 μCi of $^{64}$Cu-LO263 and imaged after 2 h, and 24 h by using Inveon small-animal PET/CT (Siemens) (FIG. 8B). Briefly, a CT anatomic image scan was acquired (80 kV, 500 μA) with a pixel size of approximately 0.1 mm. After CT imaging, whole-body PET imaging was performed with 5 min static scan. The PET images were reconstructed using the ordered-subsets expectation maximization 3-dimensional algorithm based on CT attenuation and analyzed using the Inveon Research Workplace (IRW) software (Siemens). PET voxel size was 0.796×0.861×0.861 mm, for a total of 128×128×159 voxels. Then PET/CT quantify assay was performed, and tissue radioactivity was calculated and expressed as decay-corrected percentage injected dose per gram of tissue (% ID/g). Investigators conducting the trial were blinded as to what groups were being imaged.

NMR Spectra of Synthetic Compounds

2CQ (2)

LCMS: Calculated for $C_{99}H_{108}N_{10}O_{21}S_5^{2+}$: 966.81; found; 966.8, HRMS: calculated for $C_{99}H_{108}N_1O_{21}S_5^{2+}$: 966.8159; found: 966.8121. $^1$H NMR (400 MHz, DMSO): δ 8.40-8.29 (m, 2H), 8.18 (d, J=8.4 Hz, 1H), 8.04-7.92 (m, 2H), 7.84 (s, 1H), 7.81 (s, 2H), 7.73 (dd, J=10.7, 5.6 Hz, 2H), 7.70-7.57 (m, 9H), 7.57-7.47 (m, 5H), 7.34-7.15 (m, 14H), 6.54 (t, J=10.2 Hz, 7H), 6.29 (dd, J=13.6, 7.9 Hz, 2H), 4.92 (s, 2H), 4.35 (dd, J=9.5, 7.2 Hz, 4H), 4.30-4.22 (m, 1H), 4.10 (tdd, J=12.7, 7.4, 5.6 Hz, 4H), 3.28-3.20 (m, 9H), 3.09-2.90 (m, 8H), 2.70 (d, J=2.1 Hz, 1H), 2.69-2.64 (m, 1H), 2.34-2.32 (m, 1H), 2.02 (t, J=6.6 Hz, 2H), 1.67 (s, 13H), 1.62-1.47 (m, 6H), 1.35-1.21 (m, 10H).

4CQ(3)

LCMS: Calculated for $C_{100}H_{112}N_{10}O_{21}S_5^{2+}$: 980.8; found; 980.6, HRMS: calculated for $C_{101}H_{112}N_{10}O_{21}S_5^{2+}$: 980.8315; found: 980.8264. $^1$H NMR (400 MHz, DMSO): δ 8.33 (t, J=13.0 Hz, 2H), 8.18 (dd, J=7.7, 1.1 Hz, 1H), 8.03-7.91 (m, 3H), 7.79 (s, 3H), 7.75-7.55 (m, 12H), 7.55-7.49 (m, 4H), 7.47 (d, J=8.1 Hz, 1H), 7.35-7.11 (m, 15H), 6.54 (t, J=12.5 Hz, 2H), 6.27 (dd, J=14.0, 8.0 Hz, 2H), 4.90 (s, 2H), 4.41-4.29 (m, 4H), 4.29-4.18 (m, 1H), 4.19-3.95 (m, 6H), 3.29-3.12 (m, 9H), 3.04-2.80 (m, 8H), 2.67 (ddd, J=8.8, 6.3, 5.4 Hz, 2H), 2.31 (dt, J=3.5, 1.9 Hz, 1H), 2.00 (t, J=7.0 Hz, 2H), 1.65 (s, 14H), 1.50 (dd, J=11.2, 6.4 Hz, 6H), 1.36-1.17 (m, 16H).

6CQ(4)

LCMS: Calculated for $C_{103}H_{116}N_{10}O_{21}S_5^{2+}$: 994.8; found; 994.8, HRMS: calculated for $C_{103}H_{116}N_{10}O_{21}S_5^{2+}$: 994.8472; found: 994.8444. $^1$H NMR (400 MHz, DMSO) δ 8.34 (t, J=12.9 Hz, 2H), 8.19 (d, J=9.0 Hz, 1H), 8.04-7.91 (m, 3H), 7.79 (s, 2H), 7.71 (t, J=5.5 Hz, 1H), 7.63 (ddd, J=20.6, 10.2, 5.4 Hz, 10H), 7.50 (dd, J=17.0, 7.9 Hz, 5H), 7.21 (ddt, J=23.7, 21.2, 7.0 Hz, 14H), 6.54 (t, J=12.3 Hz, 4H), 6.27 (dd, J=13.7, 7.8 Hz, 2H), 4.90 (s, 2H), 4.34 (t, J=9.9 Hz, 4H), 4.25 (dd, J=10.2, 6.0 Hz, 1H), 4.19-3.97 (m, 5H), 3.23 (dt, J=17.2, 8.7 Hz, 9H), 3.04-2.84 (m, 7H), 2.71 (d, J=12.6 Hz, 1H), 2.67-2.63 (m, 1H), 2.31 (dt, J=3.7, 1.9 Hz, 1H), 2.00 (t, J=7.1 Hz, 3H), 1.65 (s, 13H), 1.50 (t, J=11.5 Hz, 6H), 1.36-1.05 (m, 20H).

2QC(5)

LCMS: Calculated for $C_{99}H_{108}N_{10}O_{21}S_5^{2+}$: 966.81; found; 966.8, HRMS: calculated for $C_{99}H_{108}N_{10}O_{21}S_5^{2+}$: 966.8159; found: 966.8122. $^1$H NMR (400 MHz, DMSO) δ 8.33 (t, J=12.4 Hz, 2H), 8.18 (d, J=8.0 Hz, 1H), 8.07-7.91 (m, 3H), 7.90-7.84 (m, 1H), 7.79 (s, 3H), 7.70-7.57 (m, 10H), 7.50 (dd, J=18.9, 10.0 Hz, 4H), 7.23 (ddt, J=24.4, 16.0, 8.0 Hz, 14H), 6.60-6.50 (m, 2H), 6.27 (dd, J=13.4, 10.2 Hz, 2H), 4.89 (s, 2H), 4.43-4.29 (m, 4H), 4.25 (td, J=11.1, 6.0 Hz, 1H), 4.17-4.00 (m, 5H), 3.28-3.17 (m, 8H), 3.09-2.94 (m, 6H), 2.87 (dt, J=12.4, 6.4 Hz, 2H), 2.75-2.63 (m, 2H), 2.34-2.28 (m, 1H), 2.05-1.98 (m, 3H), 1.73 (s, 1H), 1.65 (s, 13H), 1.52 (s, 6H), 1.34-1.07 (m, 13H). 4QC(6)

LCMS: Calculated for $C_{101}H_{112}N_{10}O_{21}S_5^{2+}$: 980.8; found; 980.8, HRMS: calculated for $C_{101}H_{112}N_{10}O_{21}S_5^{2+}$: 980.8315; found: 980.8267. $^1$H NMR (400 MHz, DMSO) δ 8.33 (t, J=13.5 Hz, 2H), 8.18 (d, J=7.0 Hz, 1H), 8.03-7.90 (m, 3H), 7.79 (s, 3H), 7.72 (t, J=5.4 Hz, 1H), 7.68-7.56 (m, 10H), 7.52 (d, J=8.4 Hz, 4H), 7.47 (d, J=8.7 Hz, 1H), 7.23 (dq, J=24.2, 8.1 Hz, 14H), 6.55 (t, J=12.3 Hz, 3H), 6.27 (dd, J=13.8, 7.1 Hz, 2H), 4.89 (s, 2H), 4.34 (t, J=9.5 Hz, 4H), 4.22 (dd, J=16.2, 7.4 Hz, 1H), 4.16-4.00 (m, 5H), 3.28-3.15 (m, 8H), 3.07-2.90 (m, 6H), 2.86 (dd, J=11.4, 5.5 Hz, 2H), 2.74-2.63 (m, 2H), 2.43 (d, J=11.5 Hz, 2H), 2.31 (dd, J=3.5, 1.8 Hz, 1H), 1.99 (t, J=7.2 Hz, 2H), 1.65 (s, 14H), 1.57-1.43 (m, 6H), 1.36-1.17 (m, 15H).

6QC(7)

LCMS: Calculated for $C_{103}H_{116}N_{10}O_{21}S_5^{2+}$: 994.8; found; 994.8, HRMS: calculated for $C_{103}H_{116}N_{10}O_{21}S_5^{2+}$: 994.8472; found: 994.8429. $^1$H NMR (400 MHz, DMSO) δ 8.34 (t, J=13.1 Hz, 2H), 8.21-8.12 (m, 1H), 7.96 (dt, J=15.3, 8.5 Hz, 3H), 7.79 (s, 3H), 7.73-7.55 (m, 11H), 7.50 (dd, J=19.7, 8.5 Hz, 5H), 7.23 (dq, J=16.3, 7.7 Hz, 14H), 6.53 (s, 8H), 6.27 (dd, J=13.8, 5.6 Hz, 2H), 4.89 (s, 2H), 4.28 (ddd, J=19.8, 16.3, 7.2 Hz, 5H), 4.08 (ddd, J=16.0, 11.8, 6.5 Hz, 5H), 3.27-3.13 (m, 7H), 3.04-2.90 (m, 5H), 2.86 (dd, J=12.5, 5.9 Hz, 2H), 2.74-2.63 (m, 2H), 2.31 (dt, J=3.5, 1.7 Hz, 1H), 2.00 (t, J=7.0 Hz, 2H), 1.66 (s, 12H), 1.58-1.44 (m, 5H), 1.38-1.13 (m, 20H).

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A compound having the formula (II)

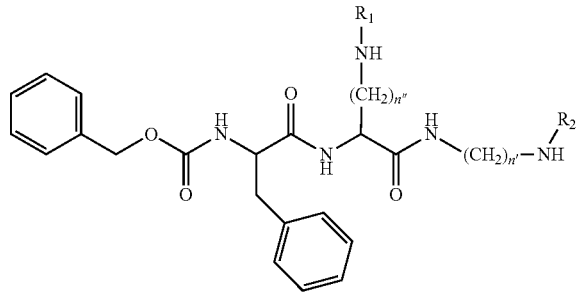

wherein
n' and n" is each independently an integer from 2-8;
$R_1$ is a QSY quencher or QC-1; and
$R_2$ is a benzopyrillium or cyanine label.

2. The compound of claim 1, wherein $R_1$ is a QSY quencher.

3. The compound of claim 1, wherein $R_1$ is QC-1.

4. The compound of claim 1, selected from the group consisting of any of the following compounds:

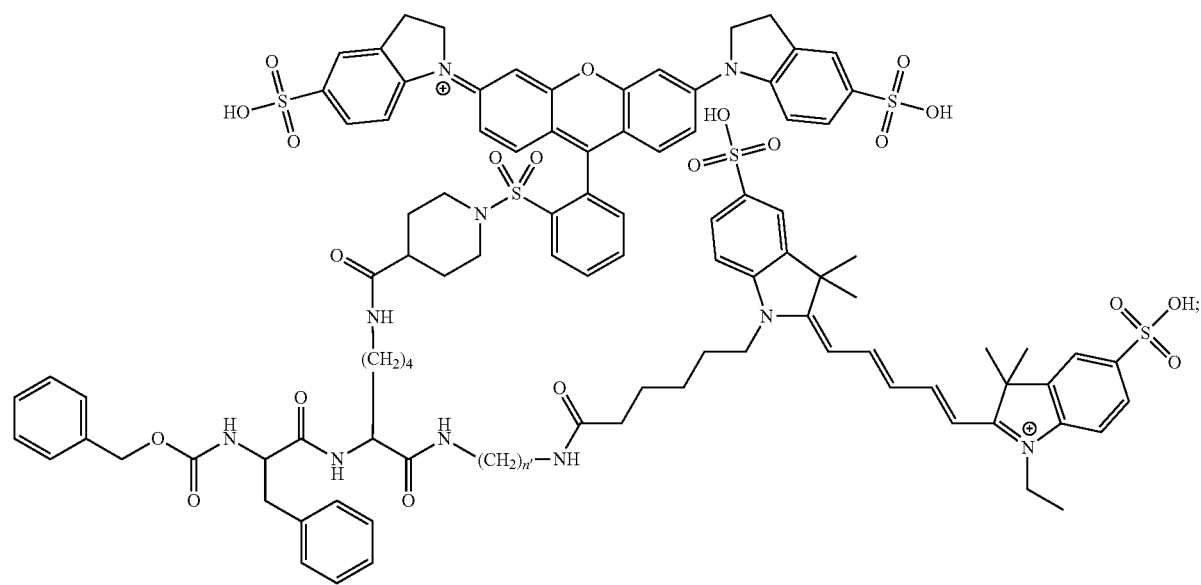
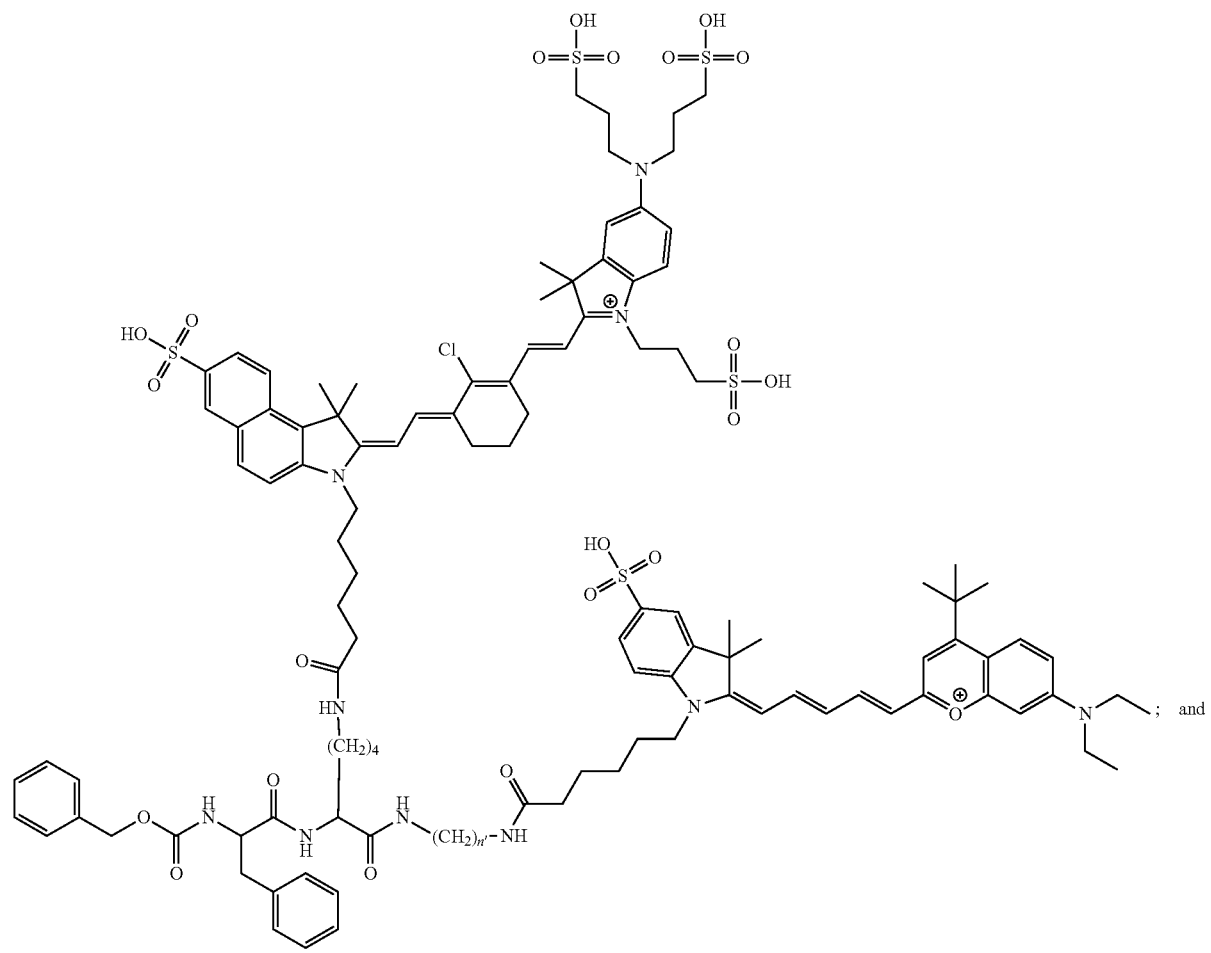

-continued

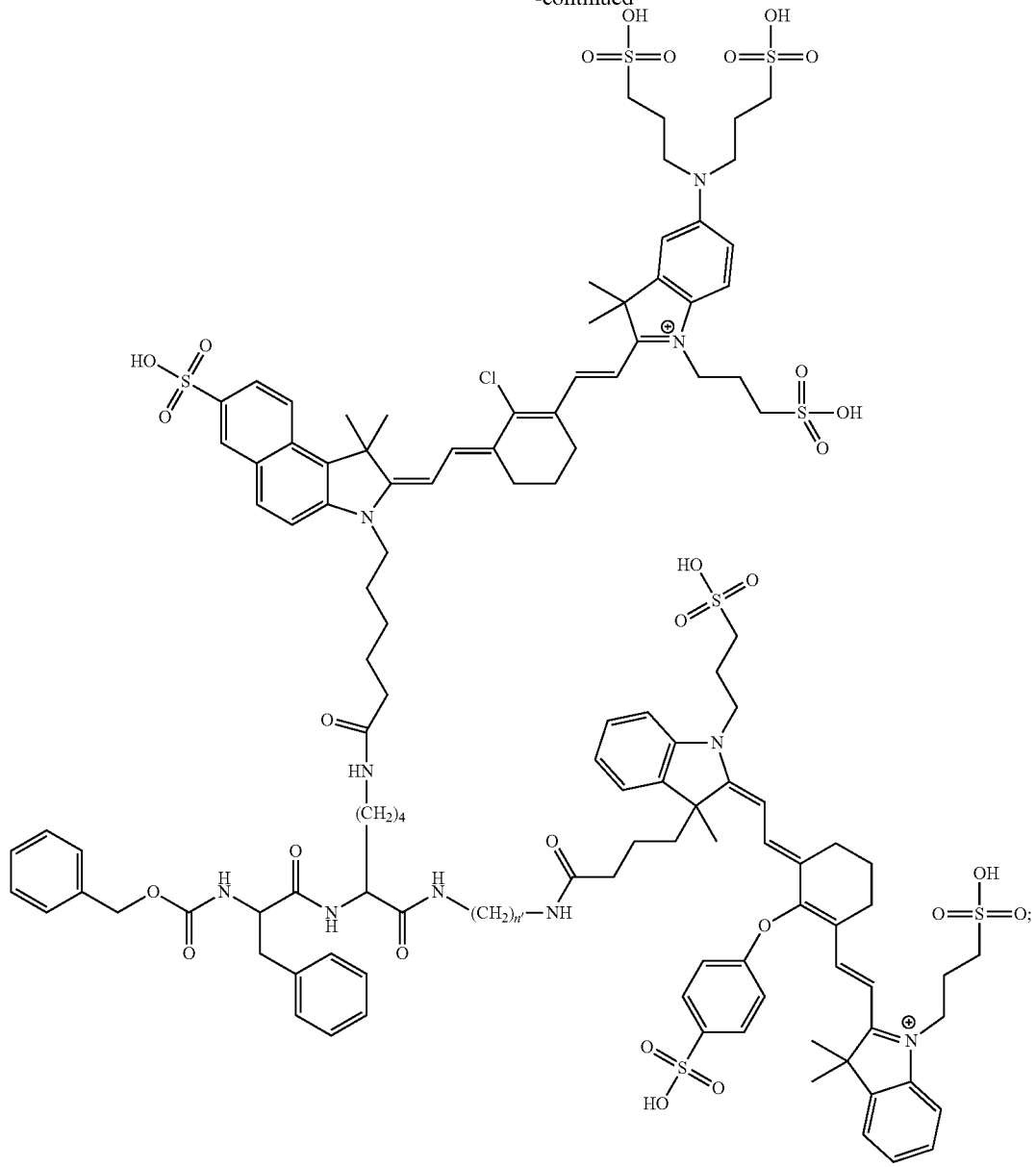

wherein n' is 2, 4, or 6; or a pharmaceutically acceptable salt thereof.

5. The compound of claim 1, wherein the benzopyrillium or cyanine label is a DyLight label.

6. The compound of claim 1, wherein the QSY quencher is a hydrophilic QSY quencher.

7. The compound of claim 6, wherein the hydrophilic QSY quencher is a sulfo-QSY quencher.

8. The compound of claim 1, wherein n" is 4.

9. The compound of claim 8, wherein n' is 2, 4, or 6.

10. A composition for use in labeling a tissue in an animal comprising a compound of claim 1 and a pharmaceutically acceptable carrier.

* * * * *